United States Patent
Wang

(10) Patent No.: US 10,172,776 B2
(45) Date of Patent: Jan. 8, 2019

(54) COMPOSITIONS FOR ALTERING THE COLOR OF HAIR

(71) Applicant: L'OREAL, Paris (FR)

(72) Inventor: Jeffrey Wang, North Brunswick, NJ (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 14/813,555

(22) Filed: Jul. 30, 2015

(65) Prior Publication Data

US 2017/0027832 A1    Feb. 2, 2017

(51) Int. Cl.
| | |
|---|---|
| A61K 8/49 | (2006.01) |
| A61Q 5/10 | (2006.01) |
| A61K 8/41 | (2006.01) |
| A61K 8/81 | (2006.01) |
| A61K 8/34 | (2006.01) |

(52) U.S. Cl.
CPC ............ *A61K 8/492* (2013.01); *A61K 8/342* (2013.01); *A61K 8/347* (2013.01); *A61K 8/411* (2013.01); *A61K 8/415* (2013.01); *A61K 8/8147* (2013.01); *A61Q 5/10* (2013.01); *A61K 2800/4324* (2013.01); *A61K 2800/48* (2013.01); *A61K 2800/882* (2013.01)

(58) Field of Classification Search
CPC ........ A61K 2800/43; A61K 2800/5424; A61K 2800/592; A61K 2800/882; A61K 8/22; A61K 8/31; A61K 8/411; A61K 8/8141; A61Q 5/10
See application file for complete search history.

(56) References Cited

U.S. PATENT DOCUMENTS

| | | | |
|---|---|---|---|
| 3,915,921 | A | 10/1975 | Schlatzer, Jr. |
| 4,003,699 | A | 1/1977 | Rose et al. |
| RE30,199 | E | 1/1980 | Rose et al. |
| 4,509,949 | A | 4/1985 | Huang et al. |
| 5,061,289 | A | 10/1991 | Clausen et al. |
| 5,380,340 | A | 1/1995 | Neunhoeffer et al. |
| 5,534,267 | A | 7/1996 | Neunhoeffer et al. |
| 5,663,366 | A | 9/1997 | Neunhoeffer et al. |
| 5,708,151 | A | 1/1998 | Mockli |
| 5,766,576 | A | 6/1998 | Lowe et al. |
| 6,099,592 | A | 8/2000 | Vidal et al. |
| 6,284,003 | B1 | 9/2001 | Rose et al. |
| 6,338,741 | B1 | 1/2002 | Vidal et al. |
| 6,645,258 | B2 | 11/2003 | Vidal et al. |
| 6,730,789 | B1 | 5/2004 | Birault et al. |
| 2002/0050013 | A1 | 5/2002 | Vidal et al. |
| 2003/0019051 | A9 | 1/2003 | Vidal et al. |

FOREIGN PATENT DOCUMENTS

| | | |
|---|---|---|
| DE | 2359399 A1 | 6/1975 |
| DE | 3843892 A1 | 6/1990 |
| DE | 4133957 A1 | 4/1993 |
| DE | 19543988 A1 | 5/1997 |
| EP | 0714954 A2 | 6/1996 |
| EP | 0770375 A1 | 5/1997 |
| FR | 2733749 A1 | 11/1996 |
| FR | 2801308 A1 | 5/2001 |
| FR | 2886136 A1 | 12/2006 |
| GB | 1026978 A | 4/1966 |
| GB | 1153196 A | 5/1969 |
| JP | 02-019576 A | 1/1990 |
| JP | 05-163124 A | 6/1993 |
| WO | 94/08969 A1 | 4/1994 |
| WO | 94/08970 A1 | 4/1994 |
| WO | 95/01772 A1 | 1/1995 |
| WO | 95/15144 A1 | 6/1995 |
| WO | 96/15765 A1 | 5/1996 |
| WO | WO 2013/144243 | * 10/2013 |

OTHER PUBLICATIONS https://www.lubrizol.com/en/Life-Sciences/Products/Carbopol-Polymer-Products. 2017.*
Todd, Charles, et al., "Volatile Silicone Fluids for Cosmetic Formulations," Cosmetics and Toiletries, vol. 91, Jan. 1976, pp. 29-32.

* cited by examiner

*Primary Examiner* — Anna R Falkowitz
(74) *Attorney, Agent, or Firm* — The Marbury Law Group, PLLC

(57) ABSTRACT

Disclosed herein is a hair treatment composition containing a polymer selected from crosslinked copolymers of (meth) acrylic acid and (C1-C6)alkyl esters, cross-linked anionic acrylate polymers, and acrylic associative polymers; a carbomer compound; a fatty alcohol that is liquid at room temperature; a fatty substance other than the fatty alcohol that is liquid at room temperature; an anionic surfactant; an amphoteric surfactant; a basic compound; a cosmetically acceptable solvent; and optionally, a colorant compound. Also disclosed is a process for altering the color of hair involving applying onto hair, a composition comprising the hair treatment composition and an oxidizing composition.

11 Claims, No Drawings

COMPOSITIONS FOR ALTERING THE COLOR OF HAIR

FIELD OF THE INVENTION

The present invention relates to a composition and process for altering the color of hair, the composition comprising a hair treatment composition containing a polymer selected from crosslinked copolymers of (meth)acrylic acid and (C1-C6)alkyl esters, cross-linked anionic acrylate polymers, and acrylic associative polymers, a carbomer, a fatty alcohol that is a liquid at room temperature and atmospheric pressure, a fatty substance other than the fatty alcohol, an anionic surfactant, an amphoteric surfactant, a basic compound, and a cosmetically acceptable solvent.

BACKGROUND OF THE INVENTION

It is known that consumers desire to use cosmetic and personal care compositions that enhance the appearance of keratin fibers such as hair by changing the color of the hair and/or by imparting various properties to hair, for example, shine and conditioning. The process of changing the color of hair can involve depositing an artificial color onto the hair which provides a different shade or color to the hair and/or lifting the color of the hair, such as lightening the color of dark hair to lighter shades.

The process of lifting the color of hair, also known as lightening, generally requires the use of compositions that comprise at least one oxidizing agent. When colorants or dye compounds such as oxidation dye precursors and direct dyes are present in these compositions, such compositions can change or deposit color and lighten the color of hair at the same time. Conventional hair coloring products are permanent dye compositions comprising oxidation dye precursors, which are also known as primary intermediates or couplers. These oxidation dye precursors are colorless or weakly colored compounds which, when combined with oxidizing agents, give rise to colored complexes by a process of oxidative condensation.

In general, hair lightening or color lifting compositions and hair dyeing compositions possess an alkalinity such that these compositions have a pH value of above 7, typically being at pH 9 and above, and may generally require the presence of basic compounds such as ammonia or an ammonia gas generating compound and/or an amine or ammonium-based compound in amounts sufficient to make such compositions alkaline. Such compounds cause the hair shaft to swell, thus allowing the small oxidative dye molecules to penetrate the cuticle and cortex before the oxidation condensation process is completed. The resulting larger-sized colored complexes from the oxidative reaction are then trapped inside the hair fiber, thereby permanently altering the color of the hair. While such hair dyeing and/or color lifting compositions can effectively alter the color of hair, these compositions can damage the hair fibers and/or irritate the scalp and may be accompanied by an undesirable odor of ammonia.

Thus, in order to reduce or avoid the drawbacks above, as well as to improve the cosmetic performance of hair color lifting and hair dyeing compositions, the use of new and additional ingredients and novel combinations of ingredients are continuously sought. However, the choice of ingredients or combinations of ingredients could pose difficulties insofar as they cannot be detrimental to other cosmetic attributes such as ease and uniformity of application, rheology or viscosity properties, stability of the compositions, color deposit and target shade formation, and/or result into more disadvantages such as increased damage, dryness, or a less healthy look to the hair. It is therefore, desirable to provide the consumer with compositions and methods that can lift the color of hair and/or deposit color onto hair in an efficient or improved manner, while providing other cosmetic advantages such as shine, conditioning, and a healthy appearance to the hair. Furthermore, it is preferable to formulate such compositions that are less costly to manufacture by requiring less and/or less costly ingredients and/or lower levels of ingredients and/or employing a more efficient process of manufacture.

Thus, the objective of the present invention is to obtain novel compositions for altering the color of hair while providing conditioning, a healthy and shiny appearance to hair and minimizing the damage to the hair and other adverse effects to the consumer. Another objective of the invention is to provide stable compositions that have a unique, non-drip consistency or rheology and yet spreads easily on the hair.

BRIEF SUMMARY OF THE INVENTION

The present disclosure is directed to compositions and processes for changing or altering the color of hair. Exemplary methods comprise applying a composition comprising a hair treatment composition and an oxidizing composition onto hair in order to deposit color onto the hair when the hair treatment composition contains a colorant and/or lift or lighten the color of the hair.

By way of example, there is a need to provide compositions and processes for coloring or dyeing hair and/or changing the hair tone (such as by lifting or lightening) while minimizing damage to the hair. Lightening or lifting the color of the hair is typically evaluated by the variation in tone height before and after the application of a hair treatment composition onto hair. This variation corresponds to the degree or level of lightening or lift. The notion of "tone" is based on the classification of the natural shades, one tone separating each shade from the shade immediately following or preceding it, which is well known to hairstyling professionals.

Accordingly, in various exemplary embodiments of the disclosure, the compositions and processes described allow one to deposit color onto hair. In further exemplary embodiments, these compositions and methods allow one to additionally achieve a desired level of color "lift" in tone, i.e. to a higher number.

In order to achieve these and other advantages, the present invention is drawn to a hair treatment composition comprising:

(a) at least one polymer selected from crosslinked copolymers of (meth)acrylic acid and (C1-C6)alkyl esters, cross-linked anionic acrylate polymers, acrylic associative polymers, and mixtures thereof;
(b) from about 0.1% to about 0.5% by weight of at least one carbomer compound;
(c) from about 0.1% to about 3% by weight of at least one fatty alcohol that is liquid at room temperature and at atmospheric pressure;
(d) at least one fatty substance other than (c);
(e) at least one anionic surfactant;
(f) at least one amphoteric surfactant;
(g) at least one basic compound selected from alkali metal carbonates, alkali metal phosphates, organic amines, hydroxide base compounds, ammonium salts, and mixtures thereof;

(h) at least one cosmetically acceptable solvent selected from water and a water/organic solvent mixture; and
(i) optionally, at least one colorant;
all weights being based on the total weight of the composition.

The present invention is also drawn to compositions for altering the color of hair comprising the above-described hair treatment composition and an oxidizing composition containing at least one oxidizing agent and a cosmetically acceptable solvent selected from water and a water/organic solvent mixture. The present invention is also drawn to a process of altering the color of hair, comprising applying onto the hair, a composition for altering the color of hair comprising the above-described hair treatment and oxidizing compositions; and leaving the composition on the hair for a period of time sufficient to alter the color of the hair. In some embodiments, the above-described hair treatment composition further comprises at least one colorant compound.

DETAILED DESCRIPTION OF THE INVENTION

Other than in the operating examples, or where otherwise indicated, all numbers expressing quantities of ingredients and/or reaction conditions are to be understood as being modified in all instances by the term "about" which encompasses ±10%.

"At least one" as used herein means one or more and thus includes individual components as well as mixtures/combinations.

"Keratin fiber" may be chosen from, for example, human hair.

The term "altering the color" and variations thereof as used herein may refer to dyeing or coloring hair or depositing color onto the hair. It can also refer to lifting or lightening the color of hair. In certain instances, it refers to lifting or lightening the color of hair and depositing color onto the hair at the same time.

"Formed from," as used herein, means obtained from chemical reaction of, wherein "chemical reaction," includes spontaneous chemical reactions and induced chemical reactions. As used herein, the phrase "formed from", is open ended and does not limit the components of the composition to those listed, e.g., as component (i) and component (ii). Furthermore, the phrase "formed from" does not limit the order of adding components to the composition or require that the listed components (e.g., components (i) and (ii)) be added to the composition before any other components.

"Hydrocarbons," as used herein, include alkanes, alkenes, and alkynes, wherein the alkanes comprise at least one carbon, and the alkenes and alkynes each comprise at least two carbons; further wherein the hydrocarbons may be chosen from linear hydrocarbons, branched hydrocarbons, and cyclic hydrocarbons; further wherein the hydrocarbons may optionally be substituted; and further wherein the hydrocarbons may optionally further comprise at least one heteroatom intercalated in the hydrocarbon chain.

"Silicone compound," as used herein, includes, for example, silica, silanes, silazanes, siloxanes, and organosiloxanes; and refers to a compound comprising at least one silicon; wherein the silicone compound may be chosen from linear silicone compounds, branched silicone compounds, and cyclic silicone compounds; further wherein the silicone compound may optionally be substituted; and further wherein the silicone compound may optionally further comprise at least one heteroatom intercalated in the silicone chain, wherein the at least one heteroatom is different from the at least one silicon.

"Substituted," as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Polymers," as defined herein, include homopolymers and copolymers formed from at least two different types of monomers.

The expression "acrylic polymer" is understood, for the purposes of the present invention, to mean a polymer that results from the polymerization of one or more monomers.

As used herein, the term "(meth)acrylic" acid and "(meth)acrylate" are meant to include the corresponding methyl derivatives of acrylic acid and the corresponding alkyl acrylate. For example, "(meth)acrylic)" acid refers to acrylic acid and/or methacrylic acid and "(meth)acrylate" refers to alkyl acrylate and/or alkyl methacrylate.

Unless otherwise indicated, the term "standard stability testing" and variations thereof, as used herein, refers to a stability test conducted on the compositions of the present invention at two months at 45° C. or up to two months at 45° C.

The term "substantially free of ammonia" as defined herein means that the compositions of the present invention are completely free of ammonia (including ammonium ions) or contains no appreciable amount of ammonia (including ammonium ions) or contains no appreciable amounts of ammonia gas generating compounds, for example, no more than 1% by weight, or no more than 0.5% by weight, or no more than 0.3% by weight, or no more than 0.1% by weight, based on the weight of the hair treatment compositions or compositions comprising the hair treatment composition and the oxidizing composition of the invention.

It has been surprisingly and unexpectedly discovered that the hair treatment composition of the present invention is stable according to standard stability testing, even when high levels of fatty substances such as oils are utilized in the composition. It has also been surprisingly and unexpectedly discovered that when the hair treatment composition of the present invention contains an oxidizing agent or when it is mixed with an oxidizing composition containing an oxidizing agent, the resulting mixture or composition is of a consistency such that it can be applied without difficulty onto hair and without running or dripping.

Moreover, it was surprisingly and unexpectedly discovered that by using the compositions of the present invention, it was possible to achieve acceptable lift to the color of the hair that corresponds to an increase in tone height of from at least 0.5 up to 3.

Furthermore, when the hair treatment composition of the present invention additionally contains colorants or dye compounds, it was surprisingly and unexpectedly discovered that said composition can be used to deposit color effectively and comparably to, if not better, than traditional or commercial hair dyes using similar or less amounts of dye compounds. Thus, the compositions and process of the present invention can provide for very good color visibility and color coverage.

It has also been surprisingly and unexpectedly found that the hair treatment composition of the invention can provide the desired cosmetic performance and attributes at lower manufacturing costs due to one or more of the following factors: lower amounts of dyes used, nature or number of ingredients, less time of production, and process of making involving a cold process method, i.e., without the use of heat.

In an embodiment, the present invention relates to a hair treatment composition containing:
(a) from about 0.6% to about 1.5% by weight of at least one polymer selected from crosslinked copolymers of (meth) acrylic acid and (C1-C6)alkyl esters, cross-linked anionic acrylate polymers, acrylic associative polymers, and mixtures thereof;
(b) from about 0.1% to about 0.3% by weight of at least one carbomer compound;
(c) from about 0.5% to about 2.5% by weight of at least one fatty alcohol that is liquid at room temperature and at atmospheric pressure;
(d) from about 40% to about 70% by weight of at least one fatty substance other than (c);
(e) from about 0.2% to about 1.5% by weight of at least one anionic surfactant;
(f) from about 0.5% to about 6% by weight of at least one amphoteric surfactant;
(g) at least about 4% by weight, of at least one basic compound selected from alkali metal carbonates, alkali metal phosphates, organic amines, hydroxide base compounds, ammonium salts, and mixtures thereof;
(h) at least one cosmetically acceptable solvent selected from water and a water/organic solvent mixture; and
(i) optionally, at least one colorant;
all weights being based on the total weight of the composition.

In another embodiment, the present invention relates to a hair treatment composition containing:
(a) from about 0.8% to about 1% by weight of at least one polymer selected from crosslinked copolymers of (meth) acrylic acid and (C1-C6)alkyl esters, cross-linked anionic acrylate polymers, acrylic associative polymers, and mixtures thereof;
(b) from about 0.14% to about 0.25% by weight of at least one carbomer compound;
(c) from about 0.5% to about 1.5% by weight of at least one fatty alcohol that is liquid at room temperature and at atmospheric pressure;
(d) from about 40% to about 60% by weight of at least one fatty substance other than (c);
(e) from about 0.45% to about 0.75% by weight of at least one anionic surfactant;
(f) from about 2% to about 3% by weight of at least one amphoteric surfactant;
(g) at least about 4% by weight, of at least one basic compound selected from alkali metal carbonates, alkali metal phosphates, organic amines, hydroxide base compounds, ammonium salts, and mixtures thereof;
(h) at least one cosmetically acceptable solvent selected from water and a water/organic solvent mixture; and
(i) optionally, at least one colorant;
all weights being based on the total weight of the composition.

In certain embodiments, the weight ratio of (b) to (d) in any one of the above-described hair treatment compositions ranges from about 0.00167 to about 0.01.

In an embodiment, the polymer (a) in any one of the above-described hair treatment compositions is chosen from crosslinked copolymers of (meth)acrylic acid and (C1-C6) alkyl esters, in particular, a crosslinked methacrylic acid/ethyl acrylate copolymer, also known as an acrylates copolymer provided as an aqueous dispersion.

In another embodiment, the fatty alcohol (c) is chosen from lauryl alcohol, oleyl alcohol, caprylic alcohol, and mixtures thereof.

In another embodiment, the fatty substance other than (c) is mineral oil.

In an embodiment, the anionic surfactant is chosen from sodium lauryl sulfate, sodium laureth sulfate, and mixtures thereof.

In another embodiment, the amphoteric surfactant is chosen from amphoacetate compounds.

In yet another embodiment, the amphoteric surfactant is chosen from betaine compounds.

The above-described hair treatment compositions may further comprise at least one colorant compound, at least one nonionic surfactant, and auxiliary/additive agents suitable for use in hair treatment compositions and compositions for altering the color of hair. The at least one colorant compound may be selected from oxidative dye precursors, direct dyes, pigments, and mixtures thereof.

The above-described hair treatment compositions are capable of being mixed with an oxidizing composition containing at least oxidizing agent selected from peroxides, urea peroxide, alkali metal bromates, ferricyanides, peroxygenated salts, perborates, percarbonates, laccases, peroxidases, redox enzymes, and mixtures thereof, and a cosmetically acceptable solvent selected from water and a water/organic solvent mixture. The resulting composition comprising the hair treatment composition and the oxidizing composition is used for lifting or lightening the composition of the hair. When the hair treatment composition additionally contains a colorant compound, the resulting composition is also used for depositing color onto hair.

In an embodiment, the present invention also relates to a composition for altering the color of hair containing any one of the above-described hair treatment compositions of the invention and the above-described oxidizing composition.

In preferred embodiments, the above-described compositions of the present invention are substantially free of ammonia or ammonia gas generating compounds.

According to another embodiment of the invention, a kit for altering the color of keratin fibers, such as hair, is provided, comprising a first unit containing any one of the above described hair treatment compositions and a second unit comprising the above described oxidizing composition.

According to other embodiments, a process for altering the color of keratin fibers, such as hair, is provided, comprising applying to the hair, a composition comprising any one of the above described hair treatment compositions and the above described oxidizing composition.

Polymer

The hair treatment composition of the present invention comprises at least one polymer selected from crosslinked copolymers of (meth)acrylic acid and (C1-C6)alkyl esters, cross-linked anionic acrylate polymers, acrylic associative polymers, and mixtures thereof.

In certain embodiments, the least one polymer of the present invention is selected from crosslinked copolymers of methacrylic acid and of a C1-C6 alkyl ester wherein the C1-C6 alkyl ester is a C1-C6 alkyl acrylate.

Methacrylic acid is preferably present in amounts ranging from 20 percent to 80 percent by weight, more particularly from 25 percent to 70 percent by weight and even more particularly from 35 percent to 65 percent by weight relative to the total weight of the copolymer.

The alkyl acrylate is preferably present in amounts ranging from 15 percent to 80 percent by weight, more particularly from 25 percent to 75 percent by weight and even more particularly from 35 percent to 65 percent by weight relative to the total weight of the copolymer. It is chosen especially from methyl acrylate, ethyl acrylate and butyl acrylate and more particularly ethyl acrylate.

This copolymer is preferably partially or totally/substantially crosslinked with at least one standard polyethylenically unsaturated crosslinking agent, for instance polyalkenyl ethers of sucrose or of polyols, diallyl phthalates, divinylbenzene, allyl (meth)acrylate, ethylene glycol di(meth)acrylate, methylenebisacrylamide, trimethylolpropane tri(meth)acrylate, diallyl itaconate, diallyl fumarate, diallyl maleate, zinc (meth)acrylate, and castor oil or polyol derivatives manufactured from unsaturated carboxylic acids. The content of crosslinking agent generally ranges from 0.01 percent to 5 percent by weight, preferably from 0.03 percent to 3 percent by weight and even more particularly from 0.05 percent to 1 percent by weight relative to the total weight of the copolymer.

In preferred embodiments, the crosslinked copolymer of methacrylic acid and of a C1-C6 alkyl acrylate is slightly cross-linked.

As used herein, the term "slightly crosslinked" refers to a partially crosslinked three-dimensional polymeric network.

In other preferred embodiments, the crosslinked copolymer of methacrylic acid and of a C1-C6 alkyl acrylate is alkali-swellable.

As used herein, the term "alkali-swellable" as it pertains to the acrylic polymer of the present invention refers to a polymer that when introduced to a solution, imparts little or no viscosity, but upon adjusting the pH to mildly acidic, neutral, or mildly basic conditions, a measurable increase in viscosity is observed, i.e., adding an alkali or neutralizing agent to a solution containing an alkali swellable polymer results in the development of viscosity.

The term "alkali-swellable" as used herein may also refer to the expansion of the polymer molecules upon neutralization as a result of charge repulsion of the anionic carboxylate groups of the polymer.

According to one particularly preferred form, the cross-linked copolymer of the invention as described above may especially be in the form of a dispersion of particles in water.

A preferred polymer of the present invention is selected from a crosslinked (meth)acrylic acid/ethyl acrylate copolymer, a cross-linked anionic acrylate polymer, and mixtures thereof.

According to one particularly preferred form, the at least one polymer of the present invention selected from a cross-linked (meth)acrylic acid/ethyl acrylate copolymer and a cross-linked anionic acrylate polymer copolymer may especially be in the form of a dispersion in water. The mean size of the copolymer particles in the dispersion is generally between 10 and 500 nm, preferably between 20 and 200 nm and more preferentially from 50 to 150 nm.

In preferred embodiments, the crosslinked (meth)acrylic acid/ethyl acrylate copolymer is a crosslinked methacrylic acid/ethyl acrylate copolymer, also known as an acrylates copolymer in aqueous dispersion, an example of which is a slightly cross-linked, alkali-swellable acrylate polymer known by the INCI name acrylates copolymer and commercially available from the supplier Lubrizol, under the tradename Carbopol® Aqua SF-1 as an aqueous dispersion comprising about 30% by weight of total solids or active material. Carbopol® Aqua SF-1 has a carboxyl functionality in its protonated form. This copolymer belongs to a class of synthetic rheology modifiers that include carboxyl functional alkali-swellable and alkali-soluble thickeners (ASTs). These thickener polymers are prepared from the free-radical polymerization of acrylic acid alone or in combination with other ethylenically unsaturated monomers. The polymers can be synthesized by solvent/precipitation as well as emulsion polymerization techniques.

Other suitable crosslinked (meth)acrylic acid/ethyl acrylate copolymers may be chosen from a crosslinked copolymer of methacrylic acid and of ethyl acrylate as an aqueous dispersion containing 38 percent active material, commercially available from the company Coatex under the name VISCOATEX™ 538C or a crosslinked copolymer of acrylic acid and of ethyl acrylate as an aqueous dispersion containing 28 percent active material, commercially available from the company Rohm and Haas and sold under the name ACULYN™ 33.

In other preferred embodiments, the at least one polymer of the present invention is a cross-linked anionic acrylate polymer. The cross-linked anionic acrylate polymer may be contained in an aqueous dispersion comprising about 32% by weight of total solids. Examples of the cross-linked anionic acrylate polymer of the present invention include, but are not limited to, the polymer known by the INCI name acrylates crosspolymer-4 and commercially available from the supplier Lubrizol, under the tradename Carbopol® Aqua SF-2, as an aqueous dispersion comprising about 32% by weight of total solids or active material. Acrylates Crosspolymer-4 may also be described as a copolymer of acrylic acid, methacrylic acid or one of its simple esters, crosslinked with trimethylolpropane triacrylate.

In certain other embodiments, the at least one polymer of the present invention is selected from acrylic associative polymers, also known as acrylic associative thickeners. The expression "associative thickener" is understood according to the invention to mean an amphiphilic thickener comprising both hydrophilic units and hydrophobic units, in particular comprising at least one C8-C30 fatty chain and at least one hydrophilic unit.

Acrylic associative thickeners that may be used according to the invention are acrylic associative polymers selected from: (i) nonionic amphiphilic polymers comprising at least one fatty chain and at least one hydrophilic unit; (ii) anionic amphiphilic polymers comprising at least one hydrophilic unit and at least one fatty-chain unit; (iii) cationic amphiphilic polymers comprising at least one hydrophilic unit and at least one fatty-chain unit; (iv) amphoteric amphiphilic polymers comprising at least one hydrophilic unit and at least one fatty-chain unit; the fatty chains containing from 10 to 30 carbon atoms.

Preferred acrylic associative polymers of the present invention are acrylic anionic amphiphilic polymers which can be selected from those comprising at least one hydrophilic unit of unsaturated olefinic carboxylic acid type, and at least one hydrophobic unit of (C10-C30) alkyl ester of an unsaturated carboxylic acid type. They are preferably selected from those in which the hydrophilic unit of unsaturated olefinic carboxylic acid type corresponds to the monomer of formula (II) below:

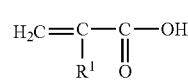

(II)

in which formula R1 denotes H or CH3 or C2H5, i.e. acrylic acid, methacrylic acid or ethacrylic acid units, and the hydrophobic unit of which, of (C10-C30)alkyl ester of an unsaturated carboxylic acid type, corresponds to the monomer of formula (III) below:

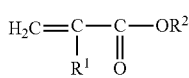

(III)

in which formula R1 denotes H or CH3 or C2H5 (i.e. acrylate, methacrylate or ethacrylate units) and preferably H (acrylate units) or CH3 (methacrylate units), R2 denoting a C10-C30 and preferably C12-C22 alkyl radical.

(C10-C30) alkyl esters of unsaturated carboxylic acids according to the invention include, for example, lauryl acrylate, stearyl acrylate, decyl acrylate, isodecyl acrylate and dodecyl acrylate, and the corresponding methacrylates, lauryl methacrylate, stearyl methacrylate, decyl methacrylate, isodecyl methacrylate and dodecyl methacrylate.

Anionic amphiphilic polymers of this type are disclosed and prepared, for example, according to the U.S. Pat. No. 3,915,921 and U.S. Pat. No. 4,509,949.

The anionic amphiphilic polymers that can be used in the context of the present invention may more particularly denote polymers formed from a mixture of monomers comprising:
(i) acrylic acid and one or more esters of formula (IV) below:

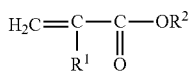

(IV)

in which R1 denotes H or CH3, R2 denoting an alkyl radical having from 12 to 22 carbon atoms, and a crosslinking agent, such as, for example, those constituted of from 95 percent to 60 percent by weight of acrylic acid (hydrophilic unit), 4 percent to 40 percent by weight of C10-C30 alkyl acrylate (hydrophobic unit), and 0 to 6 percent by weight of crosslinking polymerizable monomer, or 98 percent to 96 percent by weight of acrylic acid (hydrophilic unit), 1 percent to 4 percent by weight of C10-C30 alkyl acrylate (hydrophobic unit) and 0.1 percent to 0.6 percent by weight of crosslinking polymerizable monomer,
(ii) essentially acrylic acid and lauryl methacrylate, such as the product formed from 66 percent by weight of acrylic acid and 34 percent by weight of lauryl methacrylate.

Said crosslinking agent is a monomer containing a

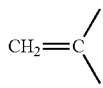

group with at least one other polymerizable group whose unsaturated bonds are not conjugated relative to one another. Mention may be made in particular of polyallyl ethers such as, in particular, polyallyl sucrose and polyallyl pentaerythritol.

Among said polymers above, the ones most particularly preferred according to the present invention are the products sold by the company Goodrich under the trade names PEMULEN™ TR1, PEMULEN™ TR2, CARBOPOL® 1382, and more preferably still PEMULEN™ TR1, and the product sold by the company Coatex under the name COATEX SM®.

In one embodiment, the at least one polymer of the present invention is selected from crosslinked copolymers of (meth)acrylic acid and/or (C1-C6)alkyl esters Thus, in some embodiments, the at least one polymer of the present invention is selected from an acrylate polymer contained in an aqueous dispersion comprising about 30% by weight of active material. This acrylate polymer may be slightly cross-linked and alkali-swellable.

In other embodiments, the at least one polymer of the present invention is selected from a cross-linked anionic acrylate polymer contained in an aqueous dispersion comprising about 32% by weight of active material.

In yet other embodiments, the at least one polymer of the present invention is chosen from a slightly cross-linked, alkali-swellable acrylate polymer contained in an aqueous dispersion comprising about 30% by weight of active material, a cross-linked anionic acrylate polymer contained in an aqueous dispersion from comprising about 32% by weight of active material, and mixtures thereof.

In some other embodiments, the at least one polymer of the present invention is chosen from acrylic associative polymers, in particular, acrylic anionic amphiphilic polymers which can be selected from those comprising at least one hydrophilic unit of unsaturated olefinic carboxylic acid type, and at least one hydrophobic unit of (C10-C30) alkyl ester of an unsaturated carboxylic acid type.

The at least one polymer of the present invention may be employed in an amount of from about 0.5% to about 2% by weight, preferably from about 0.6% to about 1.5% by weight, more preferably from about 0.7% to about 1.25% by weight and most preferably from about 0.8% to about 1% by weight, with all weights of the polymer referring to the weight of the active material and based on the total weight of the hair treatment composition of the present invention, including all ranges and subranges therebetween.

The at least one polymer of the present invention may be employed in an amount of about 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2% by weight, with the weight of the polymer referring to the weight of the active material and based on the total weight of the hair treatment composition of the present invention.

Carbomer

The hair treatment composition of the present invention comprises at least one carbomer compound.

A carbomer corresponds to a homopolymer of acrylic acid crosslinked with an allyl ether of pentaerythritol, an allyl ether of sucrose, or an allyl ether of propylene.

The carbomer of the present invention is, for example, sold under the trade name CARBOPOL 940, CARBOPOL 941, CARBOPOL 980, CARBOPOL 981, preferably CARBOPOL 981 AND CARBOPOL 980.

The carbomer of the present invention may also be known as a hydrophilic gelling polymer.

The at least one carbomer compound may be present in the composition of the present invention in an amount of from about 0.1% to about 0.5% by weight, preferably from about 0.1% to about 0.3% by weight, more preferably from about 0.13% to about 0.25% by weight and most preferably from about 0.14% to about 0.25% by weight, based on the total weight of the hair treatment composition, including all ranges and subranges therebetween.

In some embodiments, the at least one carbomer compound is employed in the composition of the present invention in an amount of about 0.1%, 0.11%, 0.12%, 0.13%, 0.15%, 0.14%, 0.15%, 0.16%, 0.17%, 0.18%, 0.19%, 0.2% and 0.25% by weight, based on the total weight of the hair treatment composition.

Liquid Fatty Alcohols

The hair treatment composition of the present invention comprises at least one fatty alcohol that is liquid at room temperature and at atmospheric pressure. The at least one fatty alcohol that is liquid at room temperature and at atmospheric pressure may also be called liquid fatty alcohols.

The term "liquid fatty alcohol" means a non-glycerolated and non-oxyalkylenated fatty alcohol, which is liquid at standard temperature (25 degrees C.) and at atmospheric pressure (760 mmHg, i.e. 1.013×105 Pa). Preferably, the liquid fatty alcohols that may be used in the composition according to the invention comprise from 6 to 40 carbon atoms such as from 8 to 30 carbon atoms or from 8 to less than 20 carbon atoms or from 8 to 16 carbon atoms or from 10 to 34 carbon atoms or from 12 to 24 carbon atoms and they may be saturated or unsaturated. The saturated liquid fatty alcohols are preferably branched. They may optionally comprise in their structure at least one aromatic or non-aromatic ring. They are preferably acyclic.

The liquid fatty alcohols of the present invention do not include fatty alcohols that are in non-liquid form such as cetyl alcohol, stearyl alcohol and a mixture thereof (cetylstearyl alcohol).

Thus, in some embodiments, the liquid fatty alcohols of the present invention, in particular C10-C34 fatty alcohols, have branched carbon-based chains or contain one or more (preferably 1 to 3) unsaturations.

In other embodiments, the liquid fatty alcohols of the present invention are preferably branched and/or unsaturated, and comprise from 12 to 40 carbon atoms. They are non-oxyalkylenated and non-glycerolated.

The liquid fatty alcohols preferably have the structure R—OH, in which R denotes a branched C6-C40 alkyl or C6-C40 alkenyl group, R possibly being substituted with one or more hydroxyl groups. Preferably, R does not contain any hydroxyl groups. Preferably, the liquid fatty alcohol is a branched saturated alcohol.

Examples that may be mentioned include oleyl alcohol, linolenyl alcohol, linoleyl alcohol, undecylenyl alcohol, palmitoleyl alcohol, erucyl alcohol, nervonyl alcohol, a-linolenyl alcohol, gamma-linolenyl alcohol, di-homo-gamma-linolenyl alcohol, arachidonyl alcohol, eicosapentaenoyl alcohol, docosahexaenoyl alcohol, isocetyl alcohol, isostearyl alcohol, 2-octyl-1-dodecanol, 2-butyloctanol, 2-hexyl-1-decanol, 2-decyl-1-tetradecanol, 2-tetradecyl-1-cetanol, caproic alcohol, caprylic alcohol, enanthic alcohol, pelargonic alcohol, and mixtures thereof.

In certain embodiments, the liquid fatty alcohol may be chosen from lauryl alcohol, oleyl alcohol, caproic alcohol, linolenyl alcohol, linoleyl alcohol, isocetyl alcohol, isostearyl alcohol, caproic alcohol, caprylic alcohol, and mixtures thereof.

More particularly, the liquid fatty alcohols that may be used in the composition according to the invention are chosen from lauryl alcohol, oleyl alcohol, caprylic alcohol, and mixtures thereof.

Lauryl alcohol is most particularly preferred.

The liquid fatty alcohols may be mixtures, that is, several species may coexist in a commercial product, especially of different chain lengths, in the form of a mixture.

The at least one liquid fatty alcohol may be present in the composition of the present invention in an amount of from about 0.1% to about 3% by weight, preferably from about 0.5% to about 2.5% by weight, more preferably from about 0.6% to about 2% by weight and most preferably from about 0.7% to about 1.5% by weight, based on the total weight of the hair treatment composition, including all ranges and subranges therebetween.

In some embodiments, the at least one liquid fatty alcohol may be present in the composition of the present invention in an amount of about 0.5%, 0.6%, 0.7%, 0.8%, 0.9%, 1%, 1.25%, 1.5%, 1.75% and 2% by weight, based on the total weight of the hair treatment composition.

Fatty Substances

The hair treatment composition of the present invention comprises at least one fatty substance other than a liquid fatty alcohol.

"Fatty substance" means an organic compound insoluble in water at normal temperature (25° C.) and at atmospheric pressure (750 mmHg) (solubility below 5% and such as below 1% and further such as below 0.1%). Fatty substances have in their structure a chain of at least two siloxane groups or at least one hydrocarbon chain having at least 6 carbon atoms. Moreover, fatty substances are generally soluble in organic solvents in the same conditions of temperature and pressure, for example in chloroform, ethanol, benzene or decamethylcyclopentasiloxane.

The method of measuring the viscosity of fatty substances such as oils and esters, can be any standard method known in the industry. Viscosity can be expressed as a kinematic viscosity or dynamic viscosity.

Fatty substances are, for example, chosen from alkanes, non-liquid fatty alcohols, esters of fatty acid, esters of fatty alcohol, oils such as mineral, vegetable, animal and synthetic non-silicone oils, non-silicone waxes and silicones.

In some embodiments, the non-liquid fatty alcohols, esters of fatty acid, and esters of fatty alcohol have at least one linear or branched, saturated or unsaturated hydrocarbon group, comprising 6 to 30 carbon atoms, optionally substituted, for example, with at least one hydroxyl group (for example 1 to 4). If they are unsaturated, these compounds can have one to three, conjugated or unconjugated, carbon-carbon double bonds.

With regard to the alkanes, in some embodiments, these have from 6 to 16 carbon atoms and are linear or branched, optionally cyclic. As examples, alkanes can be chosen from hexane and dodecane, isoparaffins such as isohexadecane, isododecane, and isodecane.

Non-limiting examples of non-silicone oils usable in the composition of the disclosure, include: hydrocarbon oils of animal origin, such as perhydrosqualene; hydrocarbon oils of vegetable origin, such as liquid triglycerides of fatty acids having from 6 to 30 carbon atoms such as triglycerides of heptanoic or octanoic acids, or for example sunflower oil, maize oil, soya oil, cucurbit oil, grapeseed oil, sesame oil, hazelnut oil, apricot oil, macadamia oil, arara oil, sunflower oil, castor oil, avocado oil, triglycerides of caprylic/capric acids such as those sold by the company Stearineries Dubois or those sold under the names MIGLYOL® 810, 812 and 818 by the company Dynamit Nobel, jojoba oil, shea butter oil; hydrocarbons with more than 16 carbon atoms, linear or branched, of mineral or synthetic origin, such as paraffin oils, petroleum jelly, liquid paraffin, polydecenes, hydrogenated polyisobutene such as Parleam®. fluorinated, partially hydrocarbon oils; as fluorinated oils, non-limiting examples include perfluoromethylcyclopentane and perfluoro-1,3-dimethylcyclohexane, sold under the names "FLUTEC®

PC1" and "FLUTEC® PC3" by the company BNFL Fluorochemicals; perfluoro-1,2-dimethylcyclobutane; perfluoroalkanes such as dodecafluoropentane and tetradecafluorohexane, sold under the names "PF 5050®" and "PF 5060®" by the 3M Company, or bromoperfluorooctyl sold under the name "FORALKYL®" by the company Atochem; nonafluoro-methoxybutane and nonafluoroethoxyisobutane; derivatives of perfluoromorpholine, such as 4-trifluoromethyl perfluoromorpholine sold under the name "PF 5052®" by the 3M Company.

The non-liquid fatty alcohols usable as fatty substances in the composition of the disclosure include, but are not limited to, non-alkoxylated, saturated or unsaturated, linear or branched, and have from 6 to 30 carbon atoms and more particularly from 8 to 30 carbon atoms; For example, cetyl alcohol, stearyl alcohol and their mixture (cetylstearyl alcohol).

The exemplary non-silicone wax or waxes that can be used in the composition of the disclosure are chosen from carnauba wax, candelilla wax, and Alfa wax, paraffin wax, ozokerite, vegetable waxes such as olive wax, rice wax, hydrogenated jojoba wax or absolute waxes of flowers such as the essential wax of blackcurrant flower sold by the company BERTIN (France), animal waxes such as beeswaxes, or modified beeswaxes (cerabellina); other waxes or waxy raw materials usable according to the disclosure are, for example, marine waxes such as that sold by the company SOPHIM under reference M82, waxes of polyethylene or of polyolefins in general.

The exemplary fatty acid esters are the esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total number of carbons of the esters being, for example, greater than or equal to 10.

Among the monoesters, non-limiting mentions can be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methyl acetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, ethyl-2-hexyl palmitate, 2-octyldecyl palmitate, alkyl myristates such as isopropyl, butyl, cetyl, 2-octyldodecyl, mirystyl, stearyl myristate, hexyl stearate, butyl stearate, isobutyl stearate; dioctyl malate, hexyl laurate, and 2-hexyldecyl laurate.

Further non-limiting mentions of esters can be made of the esters of $C_4$-$C_{22}$ di- or tricarboxylic acids and of $C_1$-$C_{22}$ alcohols and the esters of mono-, di- or tricarboxylic acids and of $C_2$-$C_{26}$ di-, tri-, tetra- or pentahydroxy alcohols.

Even further non-limiting examples of esters include: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate, tridecyl erucate; triisopropyl citrate; triisotearyl citrate; glyceryl trilactate; glyceryl trioctanoate; trioctyldodecyl citrate; trioleyl citrate, propylene glycol dioctanoate; neopentyl glycol diheptanoate; diethylene glycol diisanonate; and polyethylene glycol distearates.

Among the esters mentioned above, exemplary esters include ethyl, isopropyl, myristyl, cetyl, stearyl palmitates, ethyl-2-hexyl palmitate, 2-octyldecyl palmitate, alkyl myristates such as isopropyl, butyl, cetyl, 2-octyldodecyl myristate, hexyl stearate, butyl stearate, isobutyl stearate; dioctyl malate, hexyl laurate, 2-hexyldecyl laurate and isononyl isononanate, cetyl octanoate.

The composition can also comprise, as fatty ester, esters and di-esters of sugars of $C_6$-$C_{30}$, such as $C_{12}$-$C_{22}$ fatty acids. "Sugar" as used in the disclosure means oxygen-containing hydrocarbon compounds that possess several alcohol functions, with or without aldehyde or ketone functions, and having at least 4 carbon atoms. These sugars can be monosaccharides, oligosaccharides or polysaccharides.

As suitable sugars, non-limiting examples include sucrose, glucose, galactose, ribose, fucose, maltose, fructose, mannose, arabinose, xylose, lactose, and their derivatives, for example alkylated, such as methylated derivatives such as methylglucose.

The esters of sugars and of fatty acids can, for example, be chosen from the esters or mixtures of esters of sugars described previously and of linear or branched, saturated or unsaturated $C_6$-$C_{30}$, such as $C_{12}$-$C_{22}$ fatty acids. If they are unsaturated, these compounds can have one to three, conjugated or unconjugated, carbon-carbon double bonds.

The esters according to at least one embodiment can also be chosen from mono-, di-, tri- and tetra-esters, polyesters and mixtures thereof.

These esters can be for example oleate, laurate, palmitate, myristate, behenate, cocoate, stearate, linoleate, linolenate, caprate, arachidonates, or mixtures thereof such as the oleo-palmitate, oleo-stearate, palmito-stearate mixed esters.

For example, the mono- and di-esters can be used, and such as the mono- or di-oleate, stearate, behenate, oleopalmitate, linoleate, linolenate, oleostearate, of sucrose, of glucose or of methylglucose.

Non-limiting mention can be made of the product sold under the name GLUCATE® DO by the company Amerchol, which is a dioleate of methylglucose.

Exemplary esters or of mixtures of esters of sugar of fatty acid include: the products sold under the names F160, F140, F110, F90, F70, SL40 by the company Crodesta, denoting respectively the palmito-stearates of sucrose formed from 73% of monoester and 27% of di- and tri-ester, from 61% of monoester and 39% of di-, tri-, and tetra-ester, from 52% of monoester and 48% of di-, tri-, and tetra-ester, from 45% of monoester and 55% of di-, tri-, and tetra-ester, from 39% of monoester and 61% of di-, tri-, and tetra-ester, and the mono-laurate of sucrose; the products sold under the name Ryoto Sugar Esters for example with the reference B370 and corresponding to the behenate of sucrose formed from 20% of monoester and 80% of di-triester-polyester; sucrose mono-di-palmito-stearate marketed by the company Goldschmidt under the name TEGOSOFT® PSE.

The silicones usable in the composition of the present disclosure include but are not limited to volatile or non-volatile, cyclic, linear or branched silicones, modified or not with organic groups.

The silicones usable according to the disclosure can be in the form of oils, waxes, resins or gums.

In some embodiments, the silicone is chosen from the polydialkylsiloxanes, such as the polydimethylsiloxanes (PDMS), and the organo-modified polysiloxanes having at least one functional group selected from the poly(alkoxylated) groups, the amine groups and the alkoxy groups.

When they are volatile, the silicones are, for example, chosen from those with a boiling point between 60° C. and 260° C., and for further examples, chosen from:

the cyclic polydialkylsiloxanes having from 3 to 7, such as from 4 to 5 silicon atoms. It can be, for example, the octamethylcyclotetrasiloxane marketed under the name VOLATILE SILICONE® 7207 by UNION CARBIDE or SILBIONE® 70045 V2 by RHODIA, the decamethylcyclopentasiloxane marketed under the name VOLATILE SILICONE® 7158 by UNION CARBIDE, and SILBIONE® 70045 V5 by RHODIA, and mixtures thereof.

Non-limiting mentions can also be made of the cyclocopolymers of the dimethylsiloxanes/methylalkylsiloxane type, such as SILICONE VOLATILE® FZ 3109 marketed by the company UNION CARBIDE, of the formula I:

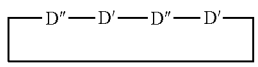

with D":

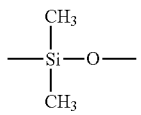

with D':

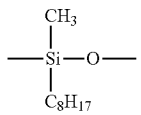

Non-limiting mentions can further be made of the mixtures of cyclic polydialkylsiloxanes with organic compounds derived from silicon, such as the mixture of octamethylcyclotetrasiloxane and tetratrimethylsilylpentaerythritol (50/50) and the mixture of octamethylcyclotetrasiloxane and oxy-1,1'-(hexa-2,2,2',2',3,3'-trimethylsilyloxy) bis-neopentane.

Other suitable volatile silicones include the linear volatile polydialkylsiloxanes having 2 to 9 silicon atoms and with a viscosity less than or equal to $5 \times 10^{-6}$ m$^2$/s at 25° C. An example is decamethyltetrasiloxane, marketed under the name "SH 200" by the company TORAY SILICONE. Silicones included in this class are also described in the article published in Cosmetics and Toiletries, Vol. 91, January 76, p. 27-32—TODD BYERS "Volatile Silicone fluids for cosmetics".

Even further non-limiting mentions can be made of non-volatile polydialkylsiloxanes, gums and resins of polydialkylsiloxanes, polyorganosiloxanes modified with the aforementioned organofunctional groups, and mixtures thereof.

These silicones are, for example, chosen from the polydialkylsiloxanes, such as the polydimethylsiloxanes with trimethylsilyl end groups. The viscosity of the silicones is measured at 25° C. according to standard ASTM 445 Appendix C.

Among these polydialkylsiloxanes, mention can be made of, non-exhaustively, the following commercial products: the SILBIONE® oils of series 47 and 70 047 or the MIRASIL® oils marketed by RHODIA, for example the oil 70 047 V 500 000; the oils of the MIRASIL® series marketed by the company RHODIA; the oils of the 200 series from the company DOW CORNING such as DC200; the VISCASIL® oils from GENERAL ELECTRIC and certain oils of the SF series (SF 96, SF 18) from GENERAL ELECTRIC.

Non-limiting mention can also be made of the polydimethylsiloxanes with dimethylsilanol end groups known under the name of dimethiconol (CTFA), such as the oils of the 48 series from the company RHODIA.

In this class of polydialkylsiloxanes, non-limiting mentions can be made of the products marketed under the names "ABIL WAX® 9800 and 9801" by the company GOLDSCHMIDT, which are polydialkyl ($C_1$-$C_{20}$) siloxanes.

The silicone gums usable according to the disclosure are, for example, polydialkylsiloxanes, such as polydimethylsiloxanes with high number-average molecular weights between 200,000 and 1,000,000 used alone or mixed in a solvent. This solvent can be chosen from the volatile silicones, the polydimethylsiloxane (PDMS) oils, the polyphenylmethylsiloxane (PPMS) oils, the isoparaffins, the polyisobutylenes, methylene chloride, pentane, dodecane, tridecane and mixtures thereof.

Products usable according to the disclosure are, for example, mixtures such as: mixtures formed from a chain end hydroxylated polydimethylsiloxane, or dimethiconol (CTFA) and a cyclic polydimethylsiloxane also called cyclomethicone (CTFA), such as the product Q2 1401 marketed by the company DOW CORNING; mixtures of a polydimethylsiloxane gum and a cyclic silicone such as the product SF 1214 Silicone Fluid from the company GENERAL ELECTRIC, said product being a gum SF corresponding to a dimethicone, having a number-average molecular weight of 500,000, dissolved in the oil SF 1202 Silicone Fluid corresponding to decamethylcyclopentasiloxane; mixtures of two PDMS of different viscosities, for example, of a PDMS gum and a PDMS oil, such as the product SF 1236 from the company GENERAL ELECTRIC. The product SF 1236 is a mixture of a gum SE 30 as defined above having a viscosity of 20 m$^2$/s and an oil SF 96 with a viscosity of $5 \times 10^{-6}$ m$^2$/s. This product, for example, has 15% of gum SE 30 and 85% of oil SF 96.

The organopolysiloxane resins usable according to the disclosure include but are not limited to crosslinked siloxane systems containing the units: $R_2SiO_{2/2}$, $R_3SiO_{1/2}$, $RSiO_{3/2}$ and $SiO_{4/2}$ in which R represents an alkyl having 1 to 16 carbon atoms. For example, R denotes a $C_1$-$C_4$ lower alkyl group such as methyl.

Among these resins, non-limiting mention can be made of the product marketed under the name "DOW CORNING 593" or those marketed under the names "SILICONE FLUID SS 4230 and SS 4267" by the company GENERAL ELECTRIC, which are silicones of dimethyl/trimethyl siloxane structure.

Non-limiting mention can also be made of the resins of the trimethylsiloxysilicate type, such as those marketed under the names X22-4914, X21-5034 and X21-5037 by the company SHIN-ETSU.

The organomodified silicones usable according to the disclosure include but are not limited to silicones as defined previously, having in their structure at least one organofunctional group fixed by a hydrocarbon group.

In addition to the silicones described above, the organomodified silicones can be polydiaryl siloxanes, such as polydiphenylsiloxanes, and polyalkyl-arylsiloxanes functionalized by the aforementioned organofunctional groups.

The polyalkarylsiloxanes are, for example, chosen from the polydimethyl/methylphenylsiloxanes, the polydimethyl/diphenylsiloxanes, linear and/or branched, with viscosity ranging from $1 \times 10^{-5}$ to $5 \times 10^{2}$ m²/s at 25° C.

Among these polyalkarylsiloxanes, non-limiting mentins can be made of the products marketed under the following names: the SILBIONE® oils of series 70 641 from RHODIA; the oils of the series RHODORSIL® 70 633 and 763 from RHODIA; the oil DOW CORNING 556 COSMETIC GRADE FLUID from DOW CORNING; the silicones of the PK series from BAYER such as the product PK20; the silicones of the series PN, PH from BAYER such as the products PN1000 and PH1000; certain oils of the SF series from GENERAL ELECTRIC such as SF 1023, SF 1154, SF 1250, SF 1265.

Among the organomodified silicones, non-limiting mention can be made of the polyorganosiloxanes having: polyoxyethylene and/or polyoxypropylene groups optionally with $C_6$-$C_{24}$ alkyl groups such as the products called dimethicone copolyol marketed by the company DOW CORNING under the name DC 1248 or the oils SILWET® L 722, L 7500, L 77, L 711 from the company UNION CARBIDE and the alkyl ($C_{12}$)-methicone copolyol marketed by the company DOW CORNING under the name Q2 5200; substituted or unsubstituted amine groups such as the products marketed under the name GP 4 Silicone Fluid and GP 7100 by the company GENESEE or the products marketed under the names Q2 8220 and DOW CORNING 929 or 939 by the company DOW CORNING. The substituted amine groups are, for example, $C_1$-$C_4$ aminoalkyl groups; alkoxylated groups, such as the product marketed under the name "SILICONE COPOLYMER F-755" by SWS SILICONES and ABIL WAX® 2428, 2434 and 2440 by the company GOLDSCHMIDT.

For example, the fatty substance is chosen from compounds that are liquid or pasty at room temperature and at atmospheric pressure.

In one embodiment, the fatty substance is a compound that is liquid at a temperature of 25° C. and at atmospheric pressure, such as for example, alkanes, esters of fatty acid, esters of fatty alcohol, hydrocarbons, silicones, non-silicone oils, and non-silicone waxes. The non-silicone oils may be selected from mineral, vegetable and synthetic oils.

According to at least one embodiment, the fatty substance is chosen from liquid paraffin, polydecenes, liquid esters of fatty acids and esters of fatty alcohols, and mixtures thereof.

In some embodiments, the fatty substance is chosen from alkanes, hydrocarbons and silicones.

The liquid fatty substances are advantageously chosen from $C_6$-$C_{16}$ alkanes such as isododecane, non-silicone oils of plant, mineral or synthetic origin, liquid fatty acids and liquid esters of a fatty acid and/or of a fatty alcohol, or mixtures thereof.

Preferably, the liquid fatty substance is chosen from liquid petroleum jelly, $C_6$-$C_{16}$ alkanes, polydecenes, liquid esters of a fatty acid and/or of a fatty alcohol, or mixtures thereof.

In some embodiments, the preferred liquid fatty substance for use in the present invention is mineral oil which may be commercially available from the supplier Exxonmobil Chemical under the tradename MARCOL 82 or from Sonneborn under the tradename KAYDOL® Heavy White Mineral Oil or from Exxonmobil Chemical under the tradename PRIMOL® 352 or from Sonneborn under the tradenames BLANDOL OR KLEAROL, or from Armedsa under the tradename AEMOIL M-302CG.

In certain embodiments, the at least one fatty substance has a viscosity of about 50 mm/s or less at 40° C. (kinematic viscosity as measured by the ASTM D 445 method in units of mm/s at 40° C.)

In other embodiments, the at least one fatty substance has a viscosity of greater than about 50 mm/s at 40° C. and may be chosen from oils such as mineral oil (kinematic viscosity as measured by the ASTM D 445 method in units of mm/s at 40° C.). One example is mineral oil with a viscosity ranging from about 63 to about 70 mm/s at 40° C., commercially available from the supplier Sonneborn under the tradename KAYDOL® Heavy White Mineral Oil or from the supplier Exxonmobil Chemical under the tradename PRIMOL® 352.

In some other embodiments, the at least one fatty substance has a viscosity of less than about 20 mm/s at 40° C. and may be chosen from oils such as mineral oil having a viscosity of about 14.5 m/s to about 17.5 mm/s at 40° C., or a viscosity of about 12 mm/s at 40° C., or a viscosity of about 7 to about 10 mm/s at 40° C. (kinematic viscosity as measured by the ASTM D 445 method in units of mm/s at 40° C.)

In certain other embodiments, the at least one fatty substance is chosen from mineral oil having a viscosity of about 14.5 mm/s to about 17.5 mm/s at 40° C. which may be commercially available from the supplier Exxonmobil Chemical under the tradename MARCOL 82.

The at least one fatty substance of the present invention may be employed in an amount of at least about 10% by weight relative to the total weight of the hair treatment composition. For example, the amount of the at least one fatty substance may be from about 40% to about 70% by weight, preferably from about 40% to about 65% by weight, more preferably from about 40% to about 60% by weight and even more preferably from about 50% to about 60% by weight, such as from about 50% to about 55% by weight or from about 50% to about 52% by weight, or from about 55% to about 60% by weight, based on the total weight of the hair treatment composition, including all ranges and subranges therebetween.

In certain embodiments, the at least one fatty substance may be present in an amount of about 40%, 45%, 55%, 60%, 65%, and 67% by weight, based on the total weight of the hair treatment composition.

In some embodiments, when the amount of fatty substances is at about 50% or more by weight, based on the total weight of the hair treatment composition, then the hair treatment composition is in the form of a cream.

In other embodiments, when the amount of fatty substances is less than about 50% by weight, based on the total weight of the hair treatment composition, then the hair treatment composition is in the form of a liquid-cream.

In yet other embodiments, when the amount of fatty substances is from about 40% to 45% by weight, based on the total weight of the hair treatment composition, then the hair treatment composition is in the form of a liquid.

Base Compound

In preferred embodiments, the at least one polymer chosen from crosslinked copolymers of (meth)acrylic acid and (C1-C6)alkyl esters, cross-linked anionic acrylate polymers, acrylic associative polymers, and mixtures thereof is neutralized in water or in an aqueous solution with a base compound before the polymer is added into the hair treatment composition of the present invention.

In other preferred embodiments, the at least one polymer is neutralized with a base compound at the time of addition of the polymer into the hair treatment composition of the present invention.

The base compound is employed in an amount sufficient to neutralize the polymer of the present invention in water or an aqueous solution. After neutralization, the polymer may be partially or fully neutralized. One indication of neutralization is the clarity of the solution.

Suitable base compounds which may be used are selected from alkali metal carbonates, alkali metal phosphates, organic amines, hydroxide base compounds, and mixtures thereof, particularly from ethylamines, ethyleneamines, alkanolamines, cyclic amines and other cyclic compounds, saturated or unsaturated, having one or more nitrogen atoms within the ring.

The organic amines may be chosen from the ones having a pKb at 25° C. of less than 12, such as less than 10 or such as less than 6. It should be noted that this is the pKb corresponding to the function of highest basicity.

Organic amines may be chosen from organic amines comprising one or two primary, secondary, or tertiary amine functions, and at least one linear or branched $C_1$-$C_8$ alkyl groups bearing at least one hydroxyl radical.

Organic amines may also be chosen from alkanolamines such as mono-, di- or trialkanolamines, comprising one to three identical or different $C_1$-$C_4$ hydroxyalkyl radicals, ethylamines, ethyleneamines, quinoline, aniline and cyclic amines, such as pyrroline, pyrrole, pyrrolidine, imidazole, imidazolidine, imidazolidinine, morpholine, pyridine, piperidine, pyrimidine, piperazine, triazine and derivatives thereof.

Among the compounds of the alkanolamine type that may be mentioned include but not limited to: monoethanolamine (also known as monoethanolamine or MEA), diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol, 2-amino-2-methyl-1-propanol, and tris(hydroxymethylamino)methane.

Other examples include but are not limited to: 1,3-diaminopropane, 1,3-diamino-2-propanol, spermine, and spermidine.

In some embodiments, the organic amines are chosen from amino acids that may be of natural or synthetic origin, in L, D, or racemic form, and comprise at least one acid function chosen from, for instance, carboxylic acid, sulfonic acid, phosphonic acid, and phosphoric acid functions. The amino acids may be in their neutral or ionic form.

Amino acids that may be used in the present disclosure include but are not limited to: aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine, and valine.

Further as non-limiting examples, the amino acids may be chosen from basic amino acids comprising an additional amine function optionally included in a ring or in a ureido function. Such basic amino acids may be chosen from histidine, lysine, arginine, ornithine, and citrulline.

In some embodiments, the organic amines are chosen from organic amines of heterocyclic type; non-limiting mention may be made of histidine, pyridine, piperidine, imidazole, 1,2,4-triazole, tetrazole, and benzimidazole.

In some embodiments, the organic amines are chosen from amino acid dipeptides, including but not limited to: carnosine, anserine, and baleine.

In some embodiments, the organic amines are chosen from compounds comprising a guanidine function. Organic amines of this type include, besides the amino acid arginine, creatine, creatinine, 1,1-dimethylguanidine, 1,1-diethylguanidine, glycocyamine, metformin, agmatine, N-amidinoalanine, 3-guanidinopropionic acid, 4-guanidinobutyric acid, and 2-([amino(imino)methyl]amino)ethane-1-sulfonic acid.

The alkali metal phosphates and carbonates that may be used are, for example, sodium phosphate, potassium phosphate, sodium carbonate, sodium bicarbonate, potassium carbonate, potassium bicarbonate, and their derivatives.

The hydroxide base compounds can be chosen from alkali metal hydroxides, alkaline-earth metal hydroxides, transition metal hydroxides, quaternary ammonium hydroxides, organic hydroxides, and mixtures thereof. Suitable examples are ammonium hydroxide, sodium hydroxide, potassium hydroxide, lithium hydroxide, rubidium hydroxide, caesium hydroxide, francium hydroxide, beryllium hydroxide, magnesium hydroxide, calcium hydroxide, strontium hydroxide, barium hydroxide, molybdenum hydroxide, manganese hydroxide, zinc hydroxide, cobalt hydroxide, cadmium hydroxide, cerium hydroxide, lanthanum hydroxide, actinium hydroxide, thorium hydroxide, aluminium hydroxide, guanidinium hydroxide and mixtures thereof.

According to at least one embodiment, the base compound of the present invention is chosen from at least one organic amine such as at least one alkanolamine. Particularly preferred alkanolamines are ethanolamine (also known as monoethanolamine or MEA), triethanolamine, and 2-amino-2-methyl-1-propanol, and mixtures thereof. An even more particularly preferred alkanolamine is ethanolamine.

The at least one base compound of the present invention may be employed in an amount of at least about 4% by weight, such as from about 4% to about 10% by weight, or such as from about 4% to about 8% by weight, or such as from about 4.5% to about 7% by weight, or such as from about 5% to about 6% by weight, based on the total weight of the hair treatment composition of the present invention, including all ranges and subranges therebetween.

The at least one base compound of the present invention may also be used to adjust the pH of the hair treatment composition as desired or needed.

Anionic Surfactants

The composition according to the invention comprises at least one anionic surfactant which may be chosen from sulfate, sulfonate and/or carboxylic (or carboxylate) surfactants, and mixtures thereof.

The term "anionic surfactant" means a surfactant comprising, as ionic or ionizable groups, only anionic groups.

In the present description, a species is termed as being "anionic" when it bears at least one permanent negative charge or when it can be ionized as a negatively charged species, under the conditions of use of the composition of the invention (for example the medium or the pH) and not comprising any cationic charge.

It is understood in the present description that:

carboxylate anionic surfactants comprise at least one carboxylic or carboxylate function (—COOH or —COO$^-$) and may optionally also comprise one or more sulfate and/or sulfonate functions;

the sulfonate anionic surfactants comprise at least one sulfonate function (—SO$_3$H or —SO$_3^-$) and may optionally also comprise one or more sulfate functions, and/or one or more carboxylate functions; and the sulfate anionic surfactants comprise at least one sulfate function and may additionally comprise carboxylate and/or sulfonate functions.

The carboxylic anionic surfactants that may be used thus comprise at least one carboxylic or carboxylate function (—COOH or —COO⁻).

They may be chosen from the following compounds: acylglycinates, acyllactylates, acylsarcosinates, acylglutamates; alkyl-D-galactosideuronic acids, alkyl ether carboxylic acids, alkyl(C6-30 aryl) ether carboxylic acids, alkylamido ether carboxylic acids; and also the salts of these compounds;

the alkyl and/or acyl groups of these compounds comprising from 6 to 30 carbon atoms, especially from 12 to 28, better still from 14 to 24 or even from 16 to 22 carbon atoms; the aryl group preferably denoting a phenyl or benzyl group;

these compounds possibly being polyoxyalkylenated, especially polyoxyethylenated, and then preferably comprising from 1 to 50 ethylene oxide units and better still from 2 to 10 ethylene oxide units.

Use may also be made of the C6-C24 alkyl monoesters of polyglycoside-polycarboxylic acids, such as C6-C24 alkyl polyglycoside-citrates, C6-C24 alkyl polyglycoside-tartrates and C6-C24 alkyl polyglycoside-sulfosuccinates, and salts thereof.

Among the above carboxylic surfactants, mention may be made most particularly of polyoxyalkylenated alkyl(amido) ether carboxylic acids and salts thereof, in particular those comprising from 2 to 50 alkylene oxide and in particular ethylene oxide groups, such as the compounds sold by the company Kao under the name Akypo, The polyoxyalkylenated alkyl (amido) ether carboxylic acids that may be used are preferably chosen from those of formula (1):

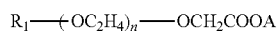

$$R_1\text{—}(OC_2H_4)_n\text{—}OCH_2COOA \quad (1)$$

in which:

R1 represents a linear or branched C6-C24 alkyl or alkenyl radical, an alkyl(C8-C9)phenyl radical, a radical R2CONH—CH2-CH2- with R2 denoting a linear or branched C9-C21 alkyl or alkenyl radical, preferably, R1 is a C8-C20 and preferably C8-C18 alkyl radical, and aryl preferably denotes phenyl, n is an integer or decimal number (average value) ranging from 2 to 24 and preferably from 2 to 10, A denotes H, ammonium, Na, K, Li, Mg or a monoethanolamine or triethanolamine residue.

It is also possible to use mixtures of compounds of formula (1), in particular mixtures of compounds containing different groups R1.

The polyoxyalkylenated alkyl(amido) ether carboxylic acids that are particularly preferred are those of formula (1) in which:

R1 denotes a C12-C14 alkyl, cocoyl, oleyl, nonylphenyl or octylphenyl radical,

A denotes a hydrogen or sodium atom, and n varies from 2 to 20 and preferably from 2 to 10.

Even more preferentially, use is made of compounds of formula (1) in which R denotes a C12 alkyl radical, A denotes a hydrogen or sodium atom and n ranges from 2 to 10.

Preferentially, the carboxylic anionic surfactants are chosen, alone or as a mixture, from:

acylglutamates, especially of C6-C24 or even C12-C20, such as stearoylglutamates, and in particular disodium stearoylglutamate;

acylsarcosinates, especially of C6-C24 or even C12-C20, such as palmitoylsarcosinates, and in particular sodium palmitoylsarcosinate;

acyllactylates, especially of C12-C28 or even C14-C24, such as behenoyllactylates, and in particular sodium behenoyllactylate;

C6-C24 and especially C12-C20 acylglycinates;

(C6-C24)alkyl ether carboxylates and especially (C12-C20)alkyl ether carboxylates;

polyoxyalkylenated ($C_6$-$C_{24}$)alkyl(amido) ether carboxylic acids, in particular those comprising from 2 to 50 ethylene oxide groups;

in particular in the form of alkali metal or alkaline-earth metal, ammonium or amino alcohol salts.

The sulfonate anionic surfactants that may be used comprise at least one sulfonate function (—SO₃H or —SO₃⁻).

In certain embodiments, the anionic surfactants may be chosen from the following compounds: alkylsulfonates, alkylamidesulfonates, alkylarylsulfonates, α-olefinsulfonates, paraffin sulfonates, alkylsulfosuccinates, alkyl ether sulfosuccinates, alkylamidesulfosuccinates, alkylsulfoacetates, N-acyltaurates, acylisethionates; alkylsulfolaurates; and also the salts of these compounds;

the alkyl groups of these compounds comprising from 6 to 30 carbon atoms, especially from 12 to 28, better still from 14 to 24 or even from 16 to 22 carbon atoms; the aryl group preferably denoting a phenyl or benzyl group;

these compounds possibly being polyoxyalkylenated, especially polyoxyethylenated, and then preferably comprising from 1 to 50 ethylene oxide units and better still from 2 to 10 ethylene oxide units.

Preferentially, the sulfonate anionic surfactants are chosen, alone or as a mixture, from:

C6-C24 and especially C12-C20 alkylsulfosuccinates, especially laurylsulfosuccinates;

C6-C24 and especially C12-C20 alkyl ether sulfosuccinates;

(C6-C24)acylisethionates and preferably (C12-C18) acylisethionates, in particular in the form of alkali metal or alkaline-earth metal, ammonium or amino alcohol salts.

The sulfate anionic surfactants that may be used comprise at least one sulfate function (—OSO₃H or —OSO₃⁻).

They may be chosen from the following compounds: alkyl sulfates, alkyl ether sulfates, alkylamido ether sulfates, alkylaryl polyether sulfates, monoglyceride sulfates; and also the salts of these compounds;

the alkyl groups of these compounds comprising from 6 to 30 carbon atoms, especially from 12 to 28, better still from 14 to 24 or even from 16 to 22 carbon atoms; the aryl group preferably denoting a phenyl or benzyl group;

these compounds possibly being polyoxyalkylenated, especially polyoxyethylenated, and then preferably comprising from 1 to 50 ethylene oxide units and better still from 2 to 10 ethylene oxide units.

Preferentially, the sulfate anionic surfactants are chosen, alone or as a mixture, from:

alkyl sulfates, especially of C6-C24 or even C12-C20, alkyl ether sulfates, especially of C6-C24 or even C12-C20, preferably comprising from 2 to 20 ethylene oxide units;

in particular in the form of alkali metal or alkaline-earth metal, ammonium or amino alcohol salts.

When the anionic surfactant is in salt form, the said salt may be chosen from alkali metal salts, such as the sodium or potassium salt, ammonium salts, amine salts and in particular amino alcohol salts, and alkaline-earth metal salts, such as the magnesium salt.

Examples of amino alcohol salts that may be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts and in particular the sodium or magnesium salts are preferably used.

Preferentially, the anionic surfactants are chosen, alone or as a mixture, from:

C6-C24 and especially C12-C20 alkyl sulfates;

C6-C24 and especially C12-C20 alkyl ether sulfates; preferably comprising from 2 to 20 ethylene oxide units;

C6-C24 and especially C12-C20 alkylsulfosuccinates, especially laurylsulfosuccinates;

C6-C24 and especially C12-C20 alkyl ether sulfosuccinates;

(C6-C24)acylisethionates and preferably (C12-C18) acylisethionates;

C6-C24 and especially C12-C20 acylsarcosinates; especially palmitoylsarcosinates;

(C6-C24)alkyl ether carboxylates, preferably (C12-C20) alkyl ether carboxylates;

polyoxyalkylenated (C6-C24)alkyl(amido) ether carboxylic acids and salts thereof, in particular those comprising from 2 to 50 alkylene oxide and in particular ethylene oxide groups;

C6-C24 and especially C12-C20 acylglutamates;

C6-C24 and especially C12-C20 acylglycinates;

in particular in the form of alkali metal or alkaline-earth metal, ammonium or amino alcohol salts.

In certain embodiments, the at least one anionic surfactant of the present invention is chosen from sulfate anionic surfactants which are chosen, alone or as a mixture, from:

alkyl sulfates, especially of C6-C24 or even C12-C20, alkyl ether sulfates, especially of C6-C24 or even C12-C20, preferably comprising from 2 to 20 ethylene oxide units;

in particular in the form of alkali metal or alkaline-earth metal, ammonium or amino alcohol salts.

In certain embodiments, the anionic surfactant of the present invention is chosen from sulfate anionic surfactants such as sodium lauryl sulfate, sodium laureth sulfate, and mixtures thereof.

The anionic surfactant(s) are preferably present in the composition in an amount ranging from about 0.1% to about 2% by weight, such as from about 0.2% to about 1.5% by weight, or preferably, from about 0.3% to about 1.25% by weight, or more preferably, from about 0.4% to about 1% by weight, or even more preferably, from about 0.45% to about 0.75% by weight, based on the total weight of the hair treatment composition of the present invention, including all ranges and subranges therebetween.

In certain embodiments, the at least one anionic surfactant may be employed according to the present invention in an amount of about 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, and 1% by weight, based on the total weight of the hair treatment composition.

Amphoteric Surfactants

The composition according to the invention comprises at least one amphoteric surfactant.

The amphoteric surfactants that may be used in the invention may be optionally quaternized secondary or tertiary aliphatic amine derivatives, in which the aliphatic group is a linear or branched chain comprising from 8 to 22 carbon atoms, said amine derivatives containing at least one anionic group, for instance a carboxylate, sulfonate, sulfate, phosphate or phosphonate group.

The at least one amphoteric surfactant may be selected from betaine compounds, amphoacetate compounds, and amphopropionate compounds such as cocoamphoacetate compounds and cocodiamphoacetate compounds, cocobetainamido amphopropionate, amphodiacetate compounds, amphodipropionate compounds, ampho-idipropionic acid compounds, sodium diethylaminopropyl cocoaspartamide, and mixtures thereof.

Mention may be made in particular of (C8-C20)alkylbetaines, sulfobetaines, (C8-C20)alkylsulfobetaines, (C8-C20)alkylamido(C1-C6)alkylbetaines, such as cocamidopropylbetaine, and (C8-C20)alkylamido(C1-C6) alkylsulfobetaines, and mixtures thereof.

Among the optionally quaternized secondary or tertiary aliphatic amine derivatives that may be used, mention may also be made of the products of respective structures (A1) and (A2) below:

$$R_a\text{—CON(Z)CH}_2\text{—(CH}_2)_m\text{—N}^+(R_b)(R_c)(CH_2COO^-) \quad (A1)$$

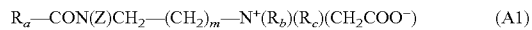

in which:

$R_a$ represents a $C_{10}$-$C_{20}$ alkyl or alkenyl group derived from an acid $R_a$—COOH preferably present in hydrolysed coconut oil, a heptyl group, a nonyl group or an undecyl group, $R_b$ represents a β-hydroxyethyl group, $R_c$ represents a carboxymethyl group;

m is equal to 0, 1 or 2,

Z represents a hydrogen atom or a hydroxyethyl or carboxymethyl group;

$$R_{a'}\text{—CON(Z)CH}_2\text{—(CH}_2)_{m'}\text{—N(B)(B')} \quad (A2)$$

in which:

B represents —$CH_2CH_2OX'$, with X' representing —$CH_2$—COOH, $CH_2$—COOZ', —$CH_2CH_2$—COOH, —$CH_2CH_2$—COOZ', or a hydrogen atom, B' represents —$(CH_2)_z$—Y', with z=1 or 2, and Y' representing —COOH, —COOZ', —$CH_2$—CHOH—$SO_3H$ or —$CH_2$—CHOH—$SO_3Z'$, m' is equal to 0, 1 or 2, Z represents a hydrogen atom or a hydroxyethyl or carboxymethyl group, Z' represents an ion resulting from an alkali or alkaline-earth metal, such as sodium, potassium or magnesium; an ammonium ion; or an ion resulting from an organic amine and in particular from an amino alcohol, such as monoethanolamine, diethanolamine and triethanolamine, monoisopropanolamine, diisopropanolamine or triisopropanolamine, 2-amino-2-methyl-1-propanol, 2-amino-2-methyl-1,3-propanediol and tris(hydroxymethyl)aminomethane, $R_{a'}$ represents a $C_{10}$-$C_{30}$ alkyl or alkenyl group of an acid $R_{a'}$COOH preferably present in hydrolysed linseed oil or coconut oil, an alkyl group, in particular a $C_{17}$ alkyl group, and its iso form, or an unsaturated $C_{17}$ group.

The compounds corresponding to formula (A2) are preferred.

Among the compounds corresponding to formula (A2) in which X' represents an hydrogen atom, mention may be made of compounds classified in the CTFA dictionary, under the names sodium cocoamphoacetate, sodium lauroamphoacetate, sodium caproamphoacetate and sodium capryloamphoacetate.

Other compounds corresponding to formula (A2) are disodium cocoamphodiacetate, disodium lauroamphodiacetate, disodium caproamphodiacetate, disodium capryloamphodiacetate, disodium cocoamphodipropionate, disodium lauroamphodipropionate, disodium caproamphodipropionate, disodium capryloamphodipropionate, lauroamphodipropionic acid and cocoamphodipropionic acid.

Examples that may be mentioned include the cocoamphodiacetate sold by the company Rhodia under the trade name MIRANOL® C2M Concentrate, the sodium cocoamphoacetate sold under the trade name MIRANOL ULTRA C 32 by the supplier Rhodia (Solvay).

Use may also be made of the compounds of formula (A3):

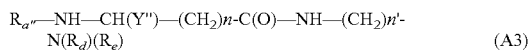

$$R_{a''}-NH-CH(Y'')-(CH_2)n\text{-}C(O)-NH-(CH_2)n'\text{-}N(R_d)(R_e) \qquad (A3)$$

in which:

$R_{a''}$ represents a $C_{10}$-$C_{30}$ alkyl or alkenyl group of an acid $R_{a''}$—C(O)OH preferably present in hydrolysed linseed oil or coconut oil;

Y" represents the group —C(O)OH, —C(O)OZ", —CH$_2$—CH(OH)—SO$_3$H or the group —CH$_2$—CH(OH)—SO$_3$—Z", with Z" representing a cationic counterion resulting from an alkali metal or alkaline-earth metal, such as sodium, an ammonium ion or an ion resulting from an organic amine;

$R_d$ and $R_e$ represent, independently of each other, a C1-C4 alkyl or hydroxyalkyl radical; and n and n' denote, independently of each other, an integer ranging from 1 to 3.

Among the compounds corresponding to formula (A3), mention may in particular be made of the compound classified in the CTFA dictionary under the name sodium diethylaminopropyl cocoaspartamide, such as the one sold by the company Chimex under the name CHIMEXANE HB.

In certain embodiments, the amphoteric surfactants of the present invention are chosen from amphoacetate compounds, in particular in the form of alkali metal or alkaline-earth metal salts, from betaine compounds, and mixtures thereof.

In some embodiments, the amphoteric surfactants are chosen from (C8-C20)alkylbetaines, (C8-C20)alkylamido(C1-C6)alkylbetaines and mixtures thereof.

In particular embodiments, the amhoteric surfactant chosen from at least one betaine is selected from cetyl betaine, lauryl betaine, cocobetaine, cocamidopropyl betaine, and mixtures thereof.

In certain embodiments, the amphoteric surfactants of the present invention are selected from amphoacetate compounds chosen from cocoamphoacetate compounds, cocoamphodiacetate compounds, in particular in the form of alkali metal or alkaline-earth metal salts, and mixtures thereof. Preferably, the amphoteric surfactant of the present invention is chosen from sodium cocoamphoacetate sold under the trade name MIRANOL ULTRA C 32 by the supplier Rhodia (Solvay).

The at least one amphoteric surfactant may be employed according to the present invention in an amount ranging from about 0.5% to about 10% by weight, such as from about 0.5% to about 8% by weight, or preferably, from about 0.5% to about 6% by weight, or more preferably, from about 1% to about 5% by weight, or even more preferably, from about 2% to about 3% by weight, based on the total weight of the hair treatment composition of the present invention, including all ranges and subranges therebetween.

In certain embodiments, the at least one amphoteric surfactant may be employed according to the present invention in an amount of about 0.5%, 0.75%, 1%, 1.25%, 1.5%, 2%, 2.25%, 2.5%, 2.75%, 3%, 3.25%, 3.5%, 3.75%, 4%, 4.25%, 4.5%, 4.75%, 5%, 5.25%, 5.5%, 5.75% and 6% by weight, based on the total weight of the hair treatment composition.

Cosmetically Acceptable Solvent

The hair treatment compositions of the present invention can comprise other compounds constituting the cosmetically acceptable solvent. This cosmetically acceptable solvent comprises water or a mixture of water and at least one cosmetically acceptable organic solvent.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol.

Other suitable examples of organic solvents are ethylene glycol, propylene glycol, butylene glycol, hexylene glycol, propane diol, and glycerin.

The organic solvents for use in the present invention can be volatile or non-volatile compounds.

The cosmetically acceptable solvent may be employed according to the present invention in an amount ranging from about 5% to about 60% by weight, or such as from about 5% to about 55% by weight, such as from about 5% to about 50% by weight, or such as from about 10% to about 35% by weight, or such as from about 10% to about 30% by weight, based on the total weight of the hair treatment composition of the present invention, including all ranges and subranges therebetween.

The organic solvent may be employed according to the present invention in an amount ranging from about 0.1% to about 25% by weight, such as from about 1% to about 15% by weight, or such as from about 3% to about 10% by weight, or such as from about 5% to about 10% by weight, based on the total weight of the hair treatment composition of the present invention, including all ranges and subranges therebetween.

Colorants

The hair treatment composition of the present invention may further comprise at least one colorant compound chosen from oxidative dye precursors, direct dyes, pigments, and mixtures thereof.

The oxidation dyes are generally chosen from one or more oxidation bases optionally combined with one or more couplers.

By way of example, the oxidation bases are chosen from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-methoxymethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, bis(ethyl)-N,N'-bis(4'-amino-3'-methylphenyl)ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases that are useful in the present invention are the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-hydroxyethoxy-3-amino-pyrazolo[1,5-a]pyridine; 2-(4-diméthylpyperazinium-1-yl)-3-amino-pyrazolo[1,5-a]pyridine; and the addition salts thereof.

More particularly oxidation bases that are useful in the present invention are selected from 3-aminopyrazolo-[1,5-a]-pyridines and preferably substituted on carbon atom 2 by:
(a) one (di) $(C_1\text{-}C_6)$ (alkyl)amino group wherein said alkyl group can be substituted by at least one hydroxy, amino, imidazolium group;
(b) one heterocycloalkyl group containing from 5 to 7 members chain, and from 1 to 3 heteroatomes, potentially cationic, potentially substituted by one or more $(C_1\text{-}C_6)$alkyl, such as di$(C_1\text{-}C_4)$alkylpipérazinium; or
(c) one $(C_1\text{-}C_6)$alkoxy potentially substituted by one or more hydroxy groups such as -hydroxyalkoxy, and the addition salts thereof.

Among the pyrimidine derivatives that may be mentioned are the compounds described, for example, in the patents DE 2359399; JP 88-169571; JP 05-63124; EP 0770375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

Among the pyrazole derivatives that may be mentioned are the compounds described in the patents DE 3843892, DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof. 4,5-Diamino-1-(β-methoxyethyl)pyrazole may also be used.

A 4,5-diaminopyrazole will preferably be used, and even more preferentially 4,5-diamino-1-(β-hydroxyethyl)pyrazole and/or a salt thereof.

Pyrazole derivatives that may also be mentioned include diamino-N,N-dihydropyrazolopyrazolones and especially those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one.

2,3-Diamino-6,7-dihydro-1H,5H-pyrazolo[1,2-a]pyrazol-1-one and/or a salt thereof will preferably be used.

4,5-Diamino-1-(β-hydroxyethyl)pyrazole and/or 2,3-diamino-6,7-dihydro-1H,5H-pyrazolo[1,2-a]pyrazol-1-one and/or a salt thereof will preferentially be used as heterocyclic bases.

Hair treatment composition according to the invention may optionally comprise one or more couplers advantageously chosen from those conventionally used in the dyeing or coloring of keratin fibers.

Among these couplers, mention may be made especially of meta-phenylenediamines, meta-aminophenols, meta-diphenols, naphthalene-based couplers and heterocyclic couplers, and also the addition salts thereof.

Mention may be made, for example, of 2-methyl-5-aminophenol, 5-N-(ß-hydroxyethyl)amino-2-methylphenol, 3-aminophenol, 5-amino-6-chloro-o-cresol (3-amino-2-chloro-6-methylphenol), 1,3-dihydroxybenzene, 1,3-dihydroxy-2-methyl-benzene, 4-chloro-1,3-dihydroxybenzene, 2,4-diamino-1-(ß-hydroxyethyloxy)benzene, 2-amino-4-(ß-hydroxyethylamino)-1-methoxybenzene, 1,3-diaminobenzene, 1,3-bis(2,4-diamino-phenoxy)propane, 3-ureidoaniline, 3-ureido-1-dimethylamino-benzene, sesamol, 1-ß-hydroxyethylamino-3,4-methylene-dioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(ß-hydroxyethyl)amino-3,4-methylene-dioxybenzene, 2,6-bis(ß-hydroxyethylamino)toluene, 6-hydroxy-indoline, 2,6-dihydroxy-4-methylpyridine, 1-H-3-methylpyrazol-5-one, 1-phenyl-3-methylpyrazol-5-one, 2,6-dimethyl-pyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In general, the addition salts of the oxidation bases and couplers that may be used in the context of the invention are especially selected from the addition salts with an acid such as the hydrochlorides, hydrobromides, sulfates, citrates, succinates, tartrates, lactates, tosylates, benzenesulfonates, phosphates and acetates.

The oxidation base(s) each advantageously represent from 0.001% to 10% by weight relative to the total weight of the composition, and preferably from 0.005% to 5% by weight relative to the total weight of the compositions of the present invention.

The coupler(s), if they are present, each advantageously represent from 0.001% to 10% by weight relative to the total weight of the composition, and preferably from 0.005% to 5% by weight relative to the total weight of the compositions of the present invention.

Compositions according to the invention may optionally comprise b) one or more synthetic or natural direct dyes, chosen from anionic and nonionic species, preferably cationic or nonionic species, either as sole dyes or in addition to the oxidation dye(s).

Examples of suitable direct dyes that may be mentioned include azo direct dyes; (poly)methine dyes such as cyanins, hemicyanins and styryls; carbonyl dyes; azine dyes; nitro (hetero)aryl dyes; tri(hetero)arylmethane dyes; porphyrin dyes; phthalocyanin dyes, and natural direct dyes, alone or as mixtures.

Preferably direct dyes are cationic direct dyes. Mention may be made of the hydrazono cationic dyes of formulas (Va) and (V'a), the azo cationic dyes (VIa) and (VI'a) and the diazo cationic dyes (VIIa) below:

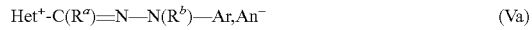  (Va)

  (V'a)

  (VIa)

  (VI'a) and

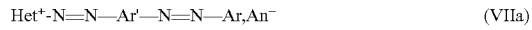  (VIIa)

in which formulas (Va), (V'a), (VIa), (VI'a) and (VIIa):

Het$^+$ represents a cationic heteroaryl radical, preferably bearing an endocyclic cationic charge, such as imidazolium, indolium or pyridinium, optionally substituted preferentially with one or more ($C_1$-$C_8$) alkyl groups such as methyl;

Ar$^+$ representing an aryl radical, such as phenyl or naphthyl, bearing an exocyclic cationic charge, preferentially ammonium, particularly tri($C_1$-$C_8$)alkylammonium such as trimethylammonium;

Ar represents an aryl group, especially phenyl, which is optionally substituted, preferentially with one or more electron-donating groups such as i) optionally substituted ($C_1$-$C_8$)alkyl, ii) optionally substituted ($C_1$-$C_8$) alkoxy, iii) (di) ($C_1$-$C_8$) (alkyl)amino optionally substituted on the alkyl group(s) with a hydroxyl group, iv) aryl($C_1$-$C_8$)alkylamino, v) optionally substituted N—($C_1$-$C_8$)alkyl-N-aryl(($C_1$-$C_8$)alkylamino or alternatively Ar represents a julolidine group;

Ar' is an optionally substituted divalent (hetero)arylene group such as phenylene, particularly para-phenylene, or naphthalene, which are optionally substituted, preferentially with one or more groups ($C_1$-$C_8$)alkyl, hydroxyl or ($C_1$-$C_8$)alkoxy;

Ar" is an optionally substituted (hetero)aryl group such as phenyl or pyrazolyl, which are optionally substituted, preferentially with one or more groups ($C_1$-$C_8$)alkyl, hydroxyl, (di) ($C_1$-$C_8$) (alkyl)amino, ($C_1$-$C_8$)alkoxy or phenyl;

$R^a$ and $R^b$, which may be identical or different, represent a hydrogen atom or a group ($C_1$-$C_8$)alkyl, which is optionally substituted, preferentially with a hydroxyl group;

or alternatively the substituent $R^a$ with a substituent of Het$^+$ and/or $R^b$ with a substituent of Ar and/or $R^a$ with $R^b$ form, together with the atoms that bear them, a (hetero)cycloalkyl;

particularly, $R^a$ and $R^b$ represent a hydrogen atom or a group ($C_1$-$C_4$)alkyl, which is optionally substituted with a hydroxyl group;

An⁻ represents an anionic counter-ion such as mesylate or halide.

In particular, mention may be made of the azo and hydrazono cationic dyes bearing an endocyclic cationic charge of formulae (Va), (V'a) and (VIa) as defined previously. More particularly those of formulae (Va), (V'a) and (VIa) derived from the dyes described in patent applications WO 95/15144, WO 95/01772 and EP-714954.

Preferentially, the cationic part is derived from the following derivatives:

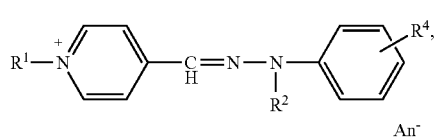
(Va-1)

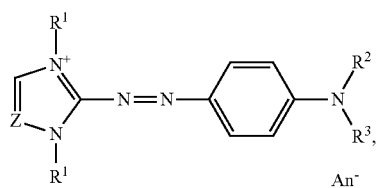
(VIa-1)

formulae (V-1) and (VI-1) with:
- $R^1$ representing a ($C_1$-$C_4$) alkyl group such as methyl;
- $R^2$ and $R^3$, which are identical or different, represent a hydrogen atom or a ($C_1$-$C_4$)alkyl group, such as methyl; and
- $R^4$ represents a hydrogen atom or an electron-donating group such as optionally substituted ($C_1$-$C_8$)alkyl, optionally substituted ($C_1$-$C_8$)alkoxy, or (di) ($C_1$-$C_8$) (alkyl)amino optionally substituted on the alkyl group(s) with a hydroxyl group; particularly, $R^4$ is a hydrogen atom,
- Z represents a CH group or a nitrogen atom, preferentially CH;
- An⁻ represents an anionic counter-ion such as mesylate or halide.

Particularly, the dye of formulae (Va-1) and (VIa-1) is chosen from Basic Red 51, Basic Yellow 87 and Basic Orange 31 or derivatives thereof:

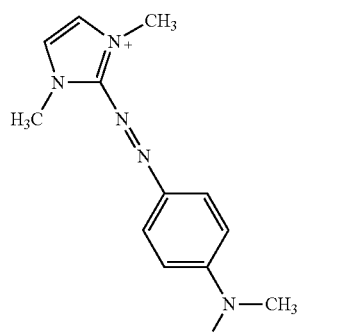

Basic Red 51

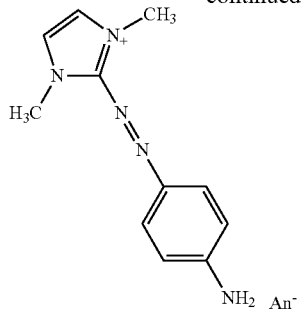

Basic Orange 31

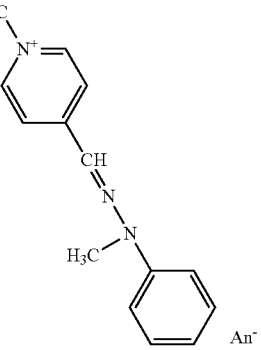

Basic Yellow 87

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin, apigenidin and orceins. Extracts or decoctions containing these natural dyes and in particular henna-based poultices or extracts may also be used.

When they are present, the direct dye(s) more particularly represent from 0.001% to 10% by weight and preferably from 0.005% to 5% by weight of the total weight of the compositions of the present invention.

Ratio of Carbomers to Fatty Substances Other than the Liquid Fatty Alcohol

In an embodiment of the present invention, the amount of the at least one polymer selected from crosslinked copolymers of (meth)acrylic acid and (C1-C6)alkyl esters, crosslinked anionic acrylate polymers, acrylic associative polymers, and mixtures thereof ranges from about 0.8% to about 1% by weight, the amount of the at least one carbomer ranges from about 0.1% to about 0.25% by weight, and the amount of the fatty substance other than the liquid fatty alcohol ranges from about 40% to about 60% by weight, all weights being based on the total weight of the hair treatment composition.

In certain embodiments, the weight ratio of the carbomer compound to the fatty substance other than the liquid fatty alcohol ranges from about 0.00167 to about 0.01 or is at about 0.00167, 0.00245, 0.0033, 0.00368, 0.0042, 0.005, 0.00625, or 0.01.

Oxidizing Agent

The present invention requires an oxidizing composition including at least one oxidizing agent which may be chosen, for example, from peroxides, persulfates, perborates percarbonates, alkali metal bromates, ferricyanides, peroxygenated salts, or a mixture thereof. Oxidizing agents that may also be used include at least one redox enzyme such as laccases, peroxidases, and 2-electron oxidoreductases, such as uricase, where appropriate in the presence of their respective donor or co-factor. Oxygen in the air may also be employed as an oxidizing agent.

In one embodiment, the oxidizing agent is hydrogen peroxide present in an aqueous solution whose titre may range from 1 to 40 volumes, such as from 5 to 40 volumes or such as from 5 to 20 volumes.

In another embodiment, the oxidizing agent is a persulfate and/or a monopersulfate such as, for example, potassium persulfate, sodium persulfate, ammonium persulfate, as well as mixtures thereof. In one embodiment, the oxidizing agents in the present disclosure are selected from hydrogen peroxide, potassium persulfate, sodium persulfate, and mixtures thereof.

In particularly preferred embodiments, the oxidizing agent is hydrogen peroxide.

In general, the oxidizing agent will be present in an amount of from about 0.05 to about 50% by weight, such as from about 0.1% to about 30% by weight, or such as from about 0.1% to about 20% by weight, or such as from about 1% to about 10% by weight, based on the total weight of the oxidizing composition.

In one particular embodiment, the oxidizing composition is aqueous or is in the form of an emulsion.

In another embodiment, the oxidizing composition is substantially anhydrous.

The term "substantially anhydrous" means that the oxidizing composition is either completely free of water or contains no appreciable amount of water, for example, no more than 5% by weight, or no more than 2% by weight, or no more than 1% by weight, based on the weight of the oxidizing composition. It should be noted that this refers for example to bound water, such as the water of crystallization of the salts or traces of water absorbed by the raw materials used in the preparation of the compositions according to the disclosure.

The oxidizing composition can contain at least one solvent, chosen from water, organic solvents, and mixtures thereof.

When the oxidizing composition is substantially anhydrous, the oxidizing composition may comprise at least one solvent chosen from organic solvents.

Suitable organic solvents for use in the oxidizing composition include ethanol, isopropyl alcohol, propanol, benzyl alcohol, phenyl ethyl alcohol, glycols and glycol ethers, such as propylene glycol, hexylene glycol, ethylene glycol monomethyl, monoethyl or monobutyl ether, propylene glycol and its ethers, such as propylene glycol monomethyl ether, butylene glycol, dipropylene glycol, diethylene glycol alkyl ethers, such as diethylene glycol monoethyl ether and monobutyl ether, ethylene glycol, propylene glycol, butylene glycol, hexylene glycol, propane diol, glycerin, hydrocarbons such as straight chain hydrocarbons, mineral oil, polybutene, hydrogenated polyisobutene, hydrogenated polydecene, polydecene, squalane, petrolatum, isoparaffins, and mixtures, thereof.

The organic solvent may, for example, be present in an amount ranging from about 0.5% to about 70% by weight, such as from about 2% to about 60% by weight, preferably from about 5 to about 50% by weight, relative to the total weight of the oxidizing composition.

The oxidizing composition may be in the form of a powder, gel, liquid, foam, lotion, cream, mousse, and emulsion.

The oxidizing composition of the present invention my also contain at least one fatty substance as described above.

Thus, the total amount of fatty substances in the combination or in the mixture of the hair treatment and oxidizing compositions of the present invention may range from about 10% to about 80% by weight, or such as from about 20% to about 60% by weight, or such as from about 20% to about 40% by weight, or such as from about 20% to about 35% by weight, based on the total weight of the mixture of the hair treatment and oxidizing compositions.

pH

The pH of the hair treatment composition of the present invention can range from about 9 to about 11, such as from about 9.5 to about 11, such as from about 9.8 to about 10.9, or such as from about 10 to about 10.5 or such as from about 10.2 to about 10.5.

The pH of the oxidizing composition can range from about 2 to about 12, such as from about 2 to about 4, and it may be adjusted to the desired value using acidifying/alkalizing agents that are well known in the art. In certain embodiments, the pH of the oxidizing composition is below 7.

The pH of the hair treatment composition and the oxidizing composition may be adjusted to the desired value using the base compounds of the present invention and/or acidifying or basifying agents that are well known in the cosmetic arts.

All numbers expressing pH values are to be understood as being modified in all instances by the term "about" which encompasses up to ±3%.

According to at least one embodiment, the hair treatment compositions and compositions comprising the hair treatment composition and the oxidizing composition of the present invention are substantially free of ammonia.

The hair treatment composition of the present disclosure is preferably in the form of an emulsion, for example, oil-in-water emulsion and water-in-oil emulsion.

In particularly preferred embodiments, the hair treatment composition of the present disclosure is preferably in the form of an oil-in-water emulsion.

The hair treatment and oxidizing compositions of the present invention may further comprise at least one auxiliary agent. The auxiliary agent may include, but is not limited to thickening agents and rheology modifying polymers other than the polymer selected from crosslinked copolymers of (meth)acrylic acid and (C1-C6)alkyl esters, cross-linked anionic acrylate polymers, acrylic associative polymers and carbomers of the present invention, cationic agents including cationic polymers, film forming polymers, humectants and moisturizing agents, emulsifying agents other than those that fall under the above-described fatty substances, fillers, structuring agents, propellants, cationic surfactants, non-ionic surfactants other than a fatty alcohol, shine agents, and conditioning agents.

Thickening agents and rheology modifying polymers other than the above-described polymer and carbomers may be chosen from polymeric thickeners and non-polymeric thickeners. The polymeric thickener can be chosen from ionic or non-ionic, associative or non-associative polymers. Exemplary polymeric thickeners include various native gums. Representative non-polymeric thickening agents include oxyethylenated molecules and especially ethoxylated alkyl or acyl derivatives of polyols. These polymers can be modified physically or chemically.

The at least one thickening agent may be employed in the compositions of the present invention in an amount of from greater than 0% to about 15% by weight, preferably from about 0.1% to about 10% by weight, and more preferably from about 1% to about 5% by weight, based on the total weight of the compositions of the present invention.

The compositions according to the present invention can also comprise at least one cationic polymer.

The cationic polymer may be chosen from cationic associative polymers comprising, in their structure, a pendent or terminal hydrophobic chain, for example of alkyl or alkenyl type, containing from 10 to 30 carbon atoms.

The at least one cationic polymer of the compositions can also be chosen from, for example:

(1) homopolymers and copolymers derived from acrylic or methacrylic esters or amides, examples of which are: copolymers of acrylamide and of dimethylaminoethyl acrylate quaternized with dimethyl sulfate or with a dimethyl halide; copolymers of acrylamide and of methacryloyloxyethyltrimethylammonium chloride; copolymer of acrylamide and of methacryloyloxyethyltrimethylammonium methosulfate; quaternized or non-quaternized vinylpyrrolidone/dialkylaminoalkyl acrylate or acrylate copolymers; dimethylaminoethyl acrylate/vinylcaprolactam/vinylpyrrolidone terpolymers; vinylpyrrolidone/methacrylamidopropyldimethylamine copolymers; quaternized vinylpyrrolidone/dimethylaminopropylmethacrylamide copolymers, and crosslinked polymers of methacryloyloxy($C_1$-$C_4$)alkyl-tri($C_1$-$C_4$)alkylammonium salts.

Other examples are cellulose ether derivatives comprising quaternary ammonium groups, such as the polymers sold under the names JR (JR 400, JR 125, JR 30M) or LR (LR 400, LR 30M) by the company Union Carbide Corporation.

(2) copolymers of cellulose or cellulose derivatives grafted with a water-soluble quaternary ammonium monomer, such as hydroxymethyl-, hydroxyethyl- or hydroxypropylcelluloses grafted, for instance, with a methacryloylethyltrimethylammonium, methacrylamidopropyltrimethylammonium or dimethyldiallylammonium salt. These are sold under the name CELQUAT L 200 and CELQUAT H 100 by the company National Starch.

(3) non-cellulose cationic polysaccharides, such as guar gums containing trialkylammonium cationic groups, such as those sold under the trade names JAGUAR C13S, JAGUAR C15, JAGUAR C17 and JAGUAR C162 by the company Meyhall.

(4) polymers of piperazinyl units and of divalent alkylene or hydroxyalkylene radicals.

(5) water-soluble polyamino amides prepared, for example, by polycondensation of an acidic compound with a polyamine.

(6) the polymers obtained by reaction of at least one polyalkylene polyamine containing two primary amine groups and at least one secondary amine group with a dicarboxylic acid chosen from diglycolic acid and saturated $C_3$-$C_8$ aliphatic dicarboxylic acids.

(7) cyclopolymers of alkyldiallylamine and of dialkyldiallylammonium, such as for example: dimethyldiallylammonium chloride homopolymer sold under the name MERQUAT® 100 and MERQUAT® 280 by the company Nalco (and its homologues of low weight-average molecular mass) and the copolymers of diallyldimethylammonium chloride and of acrylamide, sold under the name MERQUAT® 550.

(8) quaternary diammonium polymers.

(9) polyquaternary ammonium polymers.

(10) quaternary polymers of vinylpyrrolidone and of vinylimidazole, for instance the products sold under the names LUVIQUAT FC 905, FC 550 and FC 370 by the company BASF.

(11) vinylamide homopolymers or copolymers, such as partially hydrolysed vinylamide homopolymers such as poly(vinylamine/vinylamide)s.

(12) cationic polyurethane derivatives.

(13) Other cationic polymers, for example, cationic proteins or cationic protein hydrolysates, polyalkyleneimines, such as polyethyleneimines, polymers containing vinylpyridine or vinylpyridinium units, and chitin derivatives.

Particularly useful cationic polymers in the present invention include, but are not limited to, polyquaternium 4, polyquaternium 6, polyquaternium 7, polyquaternium 10, polyquaternium 11, polyquaternium 16, polyquaternium 22, polyquaternium 28, polyquaternium 32, polyquaternium-46, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-63, polyquaternium-64, polyquaternium-65, polyquaternium-66, polyquaternium-67, polyquaternium-70, polyquaternium-73, polyquaternium-74, polyquaternium-75, polyquaternium-76, polyquaternium-77, polyquaternium-78, polyquaternium-79, polyquaternium-80, polyquaternium-81, polyquaternium-82, polyquaternium-84, polyquaternium-85, polyquaternium-86, polyquaternium-87, polyquaternium-90, polyquaternium-91, polyquaternium-92, polyquaternium-94, and guar hydroxypropyltrimonium chloride (JAGUAR C® 13-S, available from Rhodia.

The cationic polymer is generally present in an amount of from greater than 0% to about 15%, preferably from about 0.5 to about 10% by weight, and more preferably from about 1 to about 5% by weight, based on the total weight of the compositions of the present invention.

The hair treatment composition of the present invention can also further comprise at least one nonionic surfactant other than a fatty alcohol. In general, nonionic surfactants having a Hydrophilic-Lipophilic Balance (HLB) of from 8 to 20, may be used in the present invention.

Examples of nonionic surfactants useful herein include, but are not limited to, alkoxylated derivatives of the following: fatty alcohols, alkyl phenols, fatty acids, fatty acid esters and fatty acid amides, wherein the alkyl chain is in the $C_{12}$-$C_{50}$ range, preferably in the $C_{16}$-$C_{40}$ range, more preferably in the $C_{24}$ to $C_{40}$ range, and having from about 1 to about 110 alkoxy groups. The alkoxy groups are selected from the group consisting of $C_2$-$C_6$ oxides and their mixtures, with ethylene oxide, propylene oxide, and their mixtures being the preferred alkoxides. The alkyl chain may be linear, branched, saturated, or unsaturated. Of these alkoxylated non-ionic surfactants, the alkoxylated alcohols are preferred, and the ethoxylated alcohols and propoxylated alcohols are more preferred. The alkoxylated alcohols may be used alone or in mixtures thereof.

Also useful herein as nonionic surfactants are alkyl glycosides, which are the condensation products of long chain alcohols, e.g. $C_8$-$C_{30}$ alcohols, with sugar or starch polymers. These compounds can be represented by the formula (S)n—O—R wherein S is a sugar moiety such as glucose, fructose, mannose, galactose, and the like; n is an integer of from about 1 to about 1000, and R is a $C_8$-$C_{30}$ alkyl group.

Other nonionic surfactants suitable for use in the present invention are glyceryl esters and polyglyceryl esters, including but not limited to, glyceryl monoesters, preferably glyceryl monoesters of $C_{16}$-$C_{22}$ saturated, unsaturated and branched chain fatty acids such as glyceryl oleate, glyceryl monostearate, glyceryl monoisostearate, glyceryl monopalmitate, glyceryl monobehenate, and mixtures thereof, and polyglyceryl esters of $C_{16}$-$C_{22}$ saturated, unsaturated and branched chain fatty acids, such as polyglyceryl-4 isostearate, polyglyceryl-oleate, polyglyceryl-2 sesquioleate, triglyceryl diisostearate, diglyceryl monooleate, tetraglyceryl monooleate, and mixtures thereof.

Also useful herein as nonionic surfactants are sorbitan esters, alkoxylated derivatives of glyceryl esters, sorbitan esters, and alkyl polyglycosides, wherein the alkoxy groups is selected from the group consisting of $C_2$-$C_6$ oxides and their mixtures, with ethoxylated or propoxylated derivatives of these materials being the preferred.

In preferred embodiments, the nonionic surfactant(s) for use in the compositions of the present invention is other than the above-described fatty substance(s) employed in said compositions.

The nonionic surfactant will typically be present in the hair treatment composition in an amount of from about 0.1% to about 30% by weight, preferably from about 0.5% to 20% by weight, and more preferably from about 1% to about 10% by weight, such as from about 1% to about 5% by weight, based on the total weight of the composition.

The compositions of the present invention according to the disclosure can also comprise at least one additive used conventionally in compositions for application onto hair.

"Additive" means a substance that is added, different from the compounds already mentioned.

As examples of additives that can be used, non-limiting mentions can be made of antioxidants or reducing agents, penetrating agents, sequestering agents, perfumes, buffers, dispersants, ceramides, sunscreen agents, preservatives, opacifiers, and antistatic agents.

The cosmetic and oxidizing compositions of the present invention according to the disclosure can be in various forms, such as in the form of liquids, creams, liquid-gels, liquid-creams, gels, lotions or pastes.

In preferred embodiments, the process of making the hair treatment composition involves a cold process that does not require the use of heat while the ingredients are mixed and does not require the use of an emulsifier blade.

According to the present disclosure, the process of making the hair treatment composition involves the following general procedure:
1. Carbomer (powder form) is added to water to prepare a carbomer gel solution. A Resoodyn cup may be used to contain the carbomer gel solution and is run at pre-determined intensity for a period of time (e.g, 4 to 5 minutes) or until the gel was uniform.
2. The carbomer gel solution is added to a beaker containing water, one or more amphoteric surfactants (e.g, Sodium Cocoamphoacetate), one or more anionic surfactants (e.g., Sodium Lauryl Sulfate), and a polymer chosen from crosslinked copolymers of (meth)acrylic acid and (C1-C6)alkyl esters, cross-linked anionic acrylate polymers, acrylic associative polymers, and mixtures thereof (eg, Acrylates Copolymer, known by the tradename Carbopol® Aqua SF-1).
3. The resulting solution in step 2 is mixed at a specific speed (e.g., 150-200 RPM) in a homogenizer for a few minutes (e.g. 6 minutes).
4. A basic compound such as ethanolamine is added to the solution while mixing until the solution turns into an opaque gel (indicates that the first polymer is neutralized).
5. A liquid fatty alcohol (e.g., Lauryl Alcohol, liquid at 25° C.) is mixed with a fatty substance (e.g., Mineral Oil) at 25° C. into a separate beaker.
6. The fatty substance mixture in step 5 is added slowly to the beaker containing the Carbomer gel mixture in step 3; the resulting mixture is mixed at high shear, high speed, for a period of time sufficient to obtain an emulsion.
7. Optional ingredients such as glycerin, dyes, antioxidants, and EDTA can be added to the mixture.

In an alternate procedure of making, the liquid fatty alcohol is added at the beginning in an amount 20 to 50% of the desired final amount in the final composition, then the rest of the liquid fatty alcohol is combined with the fatty substance (e.g., Mineral Oil), as in step 5 above.

In another alternate procedure of making, the fatty substance (e.g., Mineral oil) was added at the beginning in an amount 20 to 50% of the desired final amount in the final composition, then the rest of the fatty substance was combined with the liquid fatty alcohol as in step 5 above.

The polymer chosen from crosslinked copolymers of (meth)acrylic acid and (C1-C6)alkyl esters, cross-linked anionic acrylate polymers, acrylic associative polymers, and mixtures thereof may also be pre-neutralized before it is combined with the other ingredients according to the process above.

The above-described process is a cold process at 25° C. and atmospheric pressure, that is, it does not require heat and reduces the amount of energy and monetary cost needed to prepare a conventional/commercial hair treatment composition. It was surprisingly found that even when the fatty substance has a low viscosity (e.g, mineral oil having a kinematic viscosity of from about 14.5 to about 17.5 $mm^2/s$ at 40° C.), the hair treatment composition was stable up to two months at 45° C. (standard stability testing); i.e., there was no phase separation or change in aspect/texture and when mixed with the oxidizing composition of the present invention, the resulting mixture did not result in significant color shifts or unacceptable color changes.

Theory

Without being bound to any one theory, it is theorized that the increased emulsion stability of the compositions of the present invention can be attributed to a molecular complex formation (or interaction) between ionic surfactants such as anionic and amphoteric surfactants (e.g., sodium lauryl sulfate and sodium/disodium cocoamphacetate) and a liquid fatty alcohol having a similar carbon chain length with at least one of the ionic surfactants. For example, lauryl alcohol, caprylic alcohol or oleyl alcohol have carbon chain lengths ranging from C8 to C18 while sodium lauryl sulfate has a carbon chain length of C12. Furthermore, the liquid fatty alcohol can function as a secondary surfactant that further stabilizes the emulsion. It is also believed that the liquid fatty alcohol can help with scalp comfort by forming a barrier of protection.

It is also theorized that a surfactant blend (e.g., sodium lauryl sulfate and disodium cocoamphoacetate) allows the fatty substance of the present invention, for example mineral oil, to be processed easily in the emulsion formation. Thus, it is believed that both anionic and amphoteric surfactants in the present invention allow the oil and water to quickly interact in order to form a stable emulsion.

Without being bound to any one theory, it is also believed that due to its rheological properties, the carbomer compound of the present invention prevents oil droplet coalescence in low viscosity emulsions such as oil in water emulsions, thereby, resulting in increased stability of the emulsion. The carbomer is believed to modify the continuous phase (the water phase) by increasing the zero shear viscosity. As used herein, zero-shear viscosity refers to viscosity of a composition at the limit of low shear rate; it can also effectively refer to the viscosity of a product while at rest. For that reason, in the case of a dispersion or emulsion, an elevated continuous phase zero-shear viscosity can play a vital role in inhibiting ongoing sedimentation or creaming processes.

Process of Altering the Color of Hair

The present invention involves altering the color of hair which may be achieved when the color of hair is lifted or lightened and/or when artificial color is deposited onto hair.

Artificial color may be derived from oxidative coloration using oxidative dye precursors, or from direct coloration using direct dyes, or from temporary coloration using temporary colorants such as pigments and natural dyes.

When lifting of the color of hair is desired, the hair treatment compositions of the present invention are capable of being mixed with an oxidizing composition containing at least oxidizing agent.

When oxidative coloration on hair is to be performed, the hair treatment compositions of the present invention additionally contain a colorant chosen from oxidative dye precursors and such compositions are capable of being mixed with an oxidizing composition containing at least oxidizing agent.

The term "mixed" and all variations of this term as used herein refers to contacting or combining or reconstituting or dissolving or dispersing or blending or shaking the hair treatment composition with the oxidizing composition. It can also mean introducing the hair treatment composition to the oxidizing composition. It may also mean placing the hair treatment composition in the same vessel or container as the oxidizing composition.

Thus, the process of altering the color of hair with an oxidizing composition in accordance with the invention comprises applying a composition for altering the color of hair comprising the hair treatment composition and the oxidizing composition of the present invention onto hair. Said composition that is applied onto hair is formed by mixing the hair treatment composition with the oxidizing composition.

The hair treatment composition can be mixed or combined with the oxidizing composition in a ratio by weight of from about 1:1 to about 1:10, such as from about 1:1 to about 1:4, preferably from about 1:1 to about 1:3, or preferably from about 1:1 to about 1:2.

Upon application of the composition for altering the color of hair comprising the hair treatment composition and the oxidizing composition and after a resting time (leave-on time) on the hair, for example, ranging from about 1 to about 60 minutes, such as from about 5 to about 45 minutes, or such as from about 5 to about 20 minutes, or such as from about 10 to about 20 minutes, or such as of about 20 minutes, the hair is rinsed, optionally washed with shampoo, rinsed again, optionally washed with a hair conditioning composition, and rinsed again, then dried. The shampoo and hair conditioning composition can be any conventional hair shampoo and conditioner products.

In addition, independently of the embodiment use, the mixture or composition present on the fibers or hair (resulting from the extemporaneous mixing of the hair treatment and oxidizing compositions, or from the successive application of the hair treatment and oxidizing compositions) is left in place for a time, generally, from about 1 to about 60 minutes, such as from about 5 to about 45 minutes, or such as from about 5 to about 20 minutes, or such as from about 10 to about 20 minutes, or such as of about 20 minutes.

The temperature during the process of altering the color of hair is between room temperature and 80° C. and preferably, between room temperature and 60° C.

It has been surprisingly discovered that the combination of a polymer chosen from crosslinked copolymers of (meth) acrylic acid and (C1-C6)alkyl esters, cross-linked anionic acrylate polymers, acrylic associative polymers, and mixtures thereof, carbomer, liquid fatty alcohol, fatty substance, anionic surfactant, amphoteric surfactant and a cosmetically acceptable solvent results in a cream or liquid emulsion hair treatment composition that is stable according to standard stability testing which, when combined with the oxidizing composition of the present invention, produces a final mixture or a composition with a non-drip consistency that is still easy to spread on hair.

It has also been discovered that the application of the final mixture or composition onto the hair results in satisfactory lifting or lightening of the color of the fibers and/or coloration and shade formation on the hair when the hair treatment composition further comprises a colorant compound. At the same time, lower amounts of the oxidizing agent and/or colorant such as oxidative dye precursors and dye compounds can be used compared to conventional dyeing compositions.

The lifting of the color of the hair is evaluated by the tone height or level which describes the degree or level of lift or lightening. The tone heights range from 1 (black) to 10 (light blond), one unit corresponding to one tone; the higher the number, the lighter the shade or the greater the degree of lift.

The coloring obtained using the compositions and process of the present disclosure may also be durable or wash/fade resistant.

As used herein, the process and composition disclosed herein may be used on the hair that has not been artificially dyed or pigmented.

As used herein, the process and composition disclosed herein may be also used on the hair that has been artificially dyed or pigmented.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The examples that follow serve to illustrate embodiments of the present disclosure without, however, being limiting in nature.

EXAMPLES

The ingredient amounts in the compositions/formulas described below are expressed in % by weight, based on the total weight of the composition/formula.

Example I—Formulation Examples

TABLE 1

Inventive Hair Treatment Compositions

| US INCI NAME | Formula (% by wt) | | | | | | |
|---|---|---|---|---|---|---|---|
| | A | B | C | D | E | F | G |
| MINERAL OIL$^a$ | 50 | 50 | 50 | 50 | 50 | 50 | 50 |
| ACRYLATES COPOLYMER, (CARBOPOL ® Aqua SF-1$^b$) (30% active in water) | 3 | 3 | 3 | 3 | 3 | 3 | 3 |

TABLE 1-continued

Inventive Hair Treatment Compositions

| US INCI NAME | Formula (% by wt) | | | | | | |
|---|---|---|---|---|---|---|---|
| | A | B | C | D | E | F | G |
| CARBOMER (CARBOPOL 980$^c$) (98% active in water) | 0.15 | 0.1 | 0.15 | 0.25 | 0.2 | 0.15 | 0.15 |
| LAURYL ALCOHOL | 1 | 1 | 1.25 | 1 | 1 | — | — |
| OLEYL ALCOHOL | — | — | — | — | — | — | 1 |
| CAPRYLIC ALCOHOL | — | — | — | — | — | 1 | — |
| SODIUM COCOAMPHO-ACETATE | 3 | 3 | 3 | 3 | 3 | 3 | 3 |
| SODIUM LAURYL SULFATE | 0.55 | 0.55 | 0.55 | 0.55 | 0.55 | 0.55 | 0.55 |
| ERYTHORBIC ACID | 0.3 | 0.3 | 0.3 | 0.3 | 0.3 | 0.3 | 0.3 |
| Oxidative Dyes$^d$ | 1.90 | 1.90 | 1.90 | 1.90 | 1.90 | 1.90 | 1.90 |
| SODIUM METABISULFITE | 0.5 | 0.5 | 0.5 | 0.5 | 0.5 | 0.5 | 0.5 |
| ETHANOLAMINE | 5.32 | 5.28 | 5.32 | 5.39 | 5.35 | 5.32 | 5.32 |
| EDTA | 0.2 | 0.2 | 0.2 | 0.2 | 0.2 | 0.2 | 0.2 |
| GLYCERIN | 5 | 5 | 5 | 5 | 5 | 5 | 5 |
| FRAGRANCE | 0.8 | 0.8 | 0.8 | 0.8 | 0.8 | — | — |
| WATER | QS 100 | QS 100 | QS 100 | QS 100 | QS 100 | QS 100 | QS 100 |

$^a$viscosity of mineral oil is from about 14.5 to about 17.5 mm$^2$/s at 40° C.; mineral oil is commercially available from several suppliers such as Exxon Mobil Chemical (tradename of MARCOL 82) or Sonnenborn (tradename of BLANDOL)
$^b$commercially available from the supplier Lubrizol
$^c$commercially available from the supplier Lubrizol or Ashland
$^d$2,4-DIAMINOPHENOXYETHANOL HCl, 4-AMINO-2-HYDROXYTOLUENE 6-HYDROXYINDOLE, RESORCINOL, m-AMINOPHENOL, p-PHENYLENEDIAMINE, p-AMINOPHENOL (and) SODIUM METABISULFITE

TABLE 2

Comparative Hair Treatment Compositions

| US INCI NAME | FORMULA (% by weight) | | | | | | |
|---|---|---|---|---|---|---|---|
| | 1 | 2 | 3 | 4 | 5 | 6 | 7 |
| MINERAL OIL$^a$ | 50 | 50 | 50 | 50 | 50 | 50 | 50 |
| ACRYLATES COPOLYMER, (CARBOPOL ® Aqua SF-1$^b$) (30% active in water) | 3 | 3 | 3 | 3 | 3 | 3 | 3 |
| CARBOMER (CARBOPOL 980$^c$) (98% active in water) | — | — | — | — | 0.15 | — | — |
| CETYL ALCOHOL | 1 | 1 | 1 | — | — | — | — |
| OLEYL ALCOHOL | — | — | — | 1 | — | — | — |
| LAURYL ALCOHOL | — | — | — | — | — | 1 | — |
| DISODIUM COCOAMPHO-DIACETATE | 3 | 3 | 3 | 3 | — | — | — |
| SODIUM CETEARYL SULFATE | — | 0.55 | — | — | — | — | — |
| SODIUM COCOAMPHO-ACETATE | — | — | — | — | 3 | 3 | 3 |
| SODIUM LAURYL SULFATE | 0.55 | — | 0.55 | 0.55 | 0.55 | 0.55 | 0.55 |
| Oxidative Dyes$^d$ | 1.90 | 1.90 | 1.90 | 1.90 | 1.90 | 1.90 | 1.90 |
| ERYTHORBIC ACID | 0.3 | 0.3 | 0.3 | 0.3 | 0.3 | 0.3 | 0.3 |
| SODIUM METABISULFITE | 0.5 | 0.5 | 0.5 | 0.5 | 0.5 | 0.5 | 0.5 |
| ETHANOLAMINE | 5.20 | 5.20 | 5.20 | 5.20 | 5.32 | 5.20 | 5.20 |
| EDTA | 0.2 | 0.2 | 0.2 | 0.2 | 0.2 | 0.2 | 0.2 |
| GLYCERIN | 5 | 5 | 5 | 5 | 5 | 5 | 5 |
| ALCOHOL DENAT. | — | — | 5 | — | — | — | — |

TABLE 2-continued

Comparative Hair Treatment Compositions

| US INCI NAME | FORMULA (% by weight) | | | | | | |
|---|---|---|---|---|---|---|---|
| | 1 | 2 | 3 | 4 | 5 | 6 | 7 |
| WATER | QS 100 | QS 100 | QS 100 | QS 100 | QS 100 | QS 100 | QS 100 |

$^a$see Table 1
$^b$commercially available from the supplier Lubrizol
$^c$commercially available from the supplier Lubrizol or Ashland
$^d$2,4-DIAMINOPHENOXYETHANOL HCl, 4-AMINO-2-HYDROXYTOLUENE, 6-HYDROXYINDOLE, RESORCINOL, m-AMINOPHENOL, p-PHENYLENEDIAMINE, p-AMINOPHENOL (and) SODIUM METABISULFITE The formulas above were prepared as follows:

1. Carbomer (powder form) was added to water to prepare a carbomer gel solution. A Resoodyn cup was used to contain the carbomer gel solution and was run at predetermined intensity for 4 to 5 minutes or until the gel was uniform.

2. The carbomer gel solution was added to a beaker containing water, amphoteric surfactants (e.g, Sodium Cocoamphoacetate), anionic surfactants (e.g., Sodium Lauryl Sulfate), and a polymer chosen from crosslinked copolymers of (meth)acrylic acid and (C1-C6)alkyl esters, cross-linked anionic acrylate polymers, acrylic associative polymers, and mixtures thereof (e.g., Acrylates Copolymer, CARBOPOL® Aqua SF-1).

3. The resulting solution in step 2 was mixed at a speed of 150-200 RPM in a homogenizer for 6 minutes.

4. A basic compound such as ethanolamine was added to the solution while mixing until the solution turned into an opaque gel indicating that the acrylates copolymer was neutralized).

5. A liquid fatty alcohol was mixed with a second fatty substance, Mineral Oil, at 25° C. in a separate beaker.

6. The mixture in step 5 was added slowly to the beaker containing the Carbomer gel mixture in step 3; the resulting mixture was mixed at high shear, high speed, for a period of time sufficient to obtain an emulsion.

7. Optional ingredients such as glycerin, alcohol, dyes, antioxidants, and EDTA were added to the mixture.

In an alternate procedure of making, the liquid fatty alcohol was added at the beginning in an amount 20 to 50% of the desired final amount in the final composition, then the rest of the liquid fatty alcohol was combined with the second fatty substance (e.g., Mineral Oil), as in step 5 above.

In another alternate procedure of making, the second fatty substance (e.g., Mineral oil) was added at the beginning in an amount 20 to 50% of the desired final amount in the final composition, then the rest of the fatty substance was combined with the liquid fatty alcohol as in step 5 above.

The acrylates copolymer may also be pre-neutralized before it is combined with the other ingredients according to the process above.

The pH of the hair treatment compositions were about 10, such as about 10.34+/−5%.

If desired, the hair treatment composition can be mixed with the oxidizing composition in a weight ratio of 1:1 or 1:2 or 1:3 or 1:4. Unless specified otherwise, all ratios of hair treatment composition to oxidizing composition in the examples presented herein are 1:1 ratios.

TABLE 3

Example of an Oxidizing Composition (to be mixed with the hair treatment compositions above)

| INCI US/Ingredients | Developer formula (20 volume) % by weight |
|---|---|
| HYDROGEN PEROXIDE (50% activity in water) | 12 |
| MINERAL OIL | 20 |
| CETEARYL ALCOHOL, STEARETH-20, AND PEG-4 RAPESEEDAMIDE | 12.3 |
| OTHER INGREDIENTS: HEXADIMETHRINE CHLORIDE, POLYQUATERNIUM-6, GLYCERIN, TOCOPHEROL | 1.35 |
| SODIUM STANNATE, PENTASODIUM PENTETATE, TETRASODIUM PYROPHOSPHATE | 0.22 |
| PHOSPHORIC ACID | pH adjuster |
| WATER | QS 100 |

It was found that before mixing with an oxidizing composition, the inventive hair treatment compositions had an excellent, non-drip consistency. This consistency remained the same or changed minimally even after they were mixed with the oxidizing composition.

compositions. Viscosity in uD (units of deflection) was measured by a Mettler RM 180 Rheomat, spindle #2 (hair treatment composition) or #3 (mix composition) at 25° C.

TABLE 4

Inventive Compositions

| Time | Formula A | Formula B | Formula F | Formula G |
|---|---|---|---|---|
| | Viscosity (M2, 30 sec) [uD] | | | |
| Initial | 80.1 | 65 | 74.6 | 80.5 |
| 2 month, 25° C. | 79.1 | 69.4 | 65.6 | 73.1 |
| 2 month, 45° C. | 80.5 | 66.7 | 72.6 | 80.6 |
| 2 month, 45° C. stability | Creamy liquid; No phase separation | | | |
| | Mix Viscosity (M3, 30 sec) [uD] | | | |
| | Hair treatment composition mixed with an oxidizing composition | | | |
| Initial | 69.4 | 71.8 | 71.5 | 68.3 |
| 2 month, 25° C. | 77.5 | 75.8 | 67 | 74.6 |
| 2 month, 45° C. | 81.1 | 73.3 | 70.9 | 74.4 |

TABLE 5

Comparative Compositions

| | Formulas | | | | | | |
|---|---|---|---|---|---|---|---|
| Time | 1 | 2 | 3 | 4 | 5 | 6 | 7 |
| | Viscosity (M2, 30 sec) [uD] | | | | | | |
| Initial | 62.6 | 62.2 | 54.2 | 47.8 | 101 | 49.3 | 64.7 |
| 2 mo, 25° C. | 77.9 | N/A* | N/A | N/A | 90.5 | 54.9 | 65.6 |
| 2 mo, 45° C. | 85.2 | N/A | N/A | 49.6 | 96.5 | 57.6 | 77.8 |
| | Slight separation on bottom; congealed top layer, thickened liquid | Separation after 24 hours at 45° C. | Slight separation after 1 month 37° C. and 45° C. | Creamy liquid but separation on bottom | Creamy liquid but small oil pockets | Creamy liquid but oil pockets | Creamy liquid but separation seen |
| | Mix Viscosity (M3, 30 sec) [uD] | | | | | | |
| | Hair treatment composition mixed with an oxidizing composition | | | | | | |
| Initial | 75.9 | 65.4 | 69.3 | 56.3 | 65.3 | 74.6 | 58.5 |
| 2 mo, 25° C. | 76.8 | N/A | N/A | N/A | 73.6 | 69.7 | 69 |
| 2 mo, 45° C. | 83.3 | N/A | N/A | 63.9 | 76.4 | 71.8 | 71.5 |

*N/A = not measureable

Example II Stability

The hair treatment compositions were tested for stability. To test the stability, the compositions above were heated from between 20° C.-60° C. in a controlled environment chamber at different time points and duration for example at initial time point up to 2 months or 8 weeks. Two months at 45° C. is the standard time duration to pass stability testing (standard stability testing). The compositions were determined to be stable when there was no visible phase separation or change in aspect/texture.

The viscosities of the hair treatment compositions and mix compositions resulting from the combinations of the hair treatment compositions with an oxidizing composition were measured in order to monitor phase aspects of the compositions.

The inventive compositions remained stable and showed no phase separation and maintained their cream-like structure, even in the presence of oxidation dyes and high levels of mineral oil.

It was also observed that the inventive hair treatment compositions had no extreme changes in phase aspect, ie, there were no significant solidification, liquefaction or reduced viscosity, precipitation, solid aggregates, or vaporization. In contrast, the comparative compositions exhibited separation and oil pockets.

The viscosities of the inventive hair treatment compositions at 2 months, 45° C. generally ranged from 66.7 uD to 80.6 uD, M2, 30 sec). The viscosities of the comparative hair treatment compositions were generally either higher (85.2° C. and 96.5° C. uD) or lower (49.6° C. or 57.6° C. uD) (M2, 30 sec) at 2 months, 45° C. Comparative formula 7 had a viscosity of 77.8 uD; however phase separation was noted.

The data above also shows that, overall, there was only small variations in viscosities of the inventive hair treatment compositions and in the mix viscosities of the mix compositions at the different time and temperature points.

Example III Using Other Amphoteric Surfactants at Two Months

TABLE 6

| Temp °C. | Formula B1 (sodium cocoamphoacetate in formula B replaced with coco-betaine) | | Formula B2 (sodium cocoamphoacetate in formula B replaced with cocamidopropyl betaine) | |
|---|---|---|---|---|
| | VISCOSITY* | MIX VISCOSITY* | VISCOSITY* | MIX VISCOSITY* |
| T0/RT | 61.3 | 66.8 | 45.9 | 60.3 |
| RT | 94.2 | 70.0 | 60.9 | 65.1 |
| 37 | 77.6 | 65.4 | 55.6 | 63.5 |
| 45 | 74.0 | 66.7 | 57.9 | 66.4 |
| RT | 52.2 | 60.3 | 46.8 | 59.2 |

*Viscosity measurements taken at around 25° C., dU (M2, 30 sec)

The hair treatment compositions in Table 6 were observed to be pale pink to yellow, creamy liquids, with no phase separation; the compositions were stable at up to 2 months at 45° C. The mix compositions (1:1 of hair treatment composition to oxidizing composition) were observed to be easy to mix, resulting in smooth, fluid creams.

Example IV—Colorimetric Measurements

The mix compositions resulting from mixing the inventive and comparative hair treatment compositions were applied onto hair according to the following general procedure:

10 g of the base composition was mixed with 10 g of the oxidizing composition (1:1 ratio);
the resulting mixture or composition was applied onto hair swatches and left to stand on the hair for about 20 to 30 minutes;
the hair swatches were washed with shampoo, rinsed and dried.

For measuring the degree of change in the color of hair (e.g. degree of lightening/lifting color or color deposit) after treating the hair, the color of each swatch was measured with a Minolta CM2600d spectrocolorimeter (specular components included, 10 degrees angle, illuminant D65) in the CIEL*a*b* system.

Two parameters, L and ΔE (delta-E), were measured. L* represents the intensity of the color, a* indicates the green/red color axis and b* the blue/yellow color axis. The determination of ΔE values is based on L*, a* and b*.

According to this system, the greater the value of L, the lighter or less intense the color. Conversely, the lower the value of L, the darker or more intense the color (this can also indicate greater color deposit when the composition contains colorants).

The ΔL or the difference between the L value for the treated hair versus the L value for the control hair swatch represents a change in the value of L: the more negative the ΔL value is, the darker the color that is deposited on the hair: ΔL=Lt (treated hair)−Lc (control hair)

Delta-E (ΔE) represents color change. If ΔE is less than 1.0 there is hardly any color difference that the human eye can see. If ΔE greater than 1.0, then there is a noticeable color difference.

ΔE measurements of hair swatches treated with the mix compositions according to the method of application above were conducted at the same time points, duration and temperatures employed for the stability tests. It was found that there was no significant color shift and degree of coloration remained the same over time at room temperature and at 45 C.

In addition, in tests on hair swatches and hair on human heads of volunteers, the inventive compositions performed comparably in terms of lifting the color of hair against a first commercial oxidative hair dye and performed better in terms of post-shampoo smoothness and suppleness, ease of passing fingers and light hair against a second commercial oxidative hair dye. The inventive compositions were also observed to produce a deeper color deposit at the same dye concentrations as compared to the commercial oxidative hair dyes. Thus, it was visually observed that inventive compositions containing lower amounts of oxidative dyes compared to traditional, commercial formulations still gave comparable color deposit on hair swatches.

It was also found that the increase in the degree of lift in the hair tone was up to 2 levels.

It will be apparent to those skilled in the art that various modifications and variations can be made in the delivery system, composition and methods of the invention without departing from the spirit or scope of the invention. Thus, it is intended that the present invention cover the modifications and variations of this invention provided that they come within the scope of the appended claims and their equivalents.

What is claimed is:

1. A hair treatment composition consisting essentially of:
(a) about 3% by weight of at least one polymer chosen from acrylates copolymer selected from crosslinked copolymers of (meth)acrylic acid and ethyl acrylate;
(b) from about 0.1% to about 0.25% by weight of at least one carbomer compound chosen from homopolymers of acrylic acid crosslinked with an allyl ether of pentaerythritol, an allyl ether of sucrose, or an allyl ether of propylene;
(c) from about 1% to about 1.25% by weight of at least one fatty alcohol that is liquid at room temperature and at atmospheric pressure and chosen from lauryl alcohol, oleyl alcohol, caprylic alcohol, or mixtures thereof;
(d) about 50% by weight of at least one fatty substance other than (c) chosen from mineral oils;
(e) about 0.55% by weight of at least one anionic surfactant chosen from sodium lauryl sulfate;
(f) about 3% by weight of at least one amphoteric surfactant chosen from sodium cocoamphoacetate;
(g) from about 5% to about 6% by weight of at least one basic compound chosen from ethanolamine;
(h) at least one cosmetically acceptable solvent selected from water and a water/organic solvent mixture; and
(i) about 2.4% by weight of at least one colorant selected from oxidative dye precursors;
all weights being based on the total weight of the composition.

2. The hair treatment composition according to claim 1, wherein the crosslinked (meth)acrylic acid/ethyl acrylate copolymer is acrylates copolymer in the form of an aqueous dispersion.

3. The hair treatment composition according to claim 1, wherein the composition further comprises at least one oxidizing agent selected from peroxides, urea peroxide, alkali metal bromates, ferricyanides, peroxygenated salts, perborates, percarbonates, laccases, peroxidases, redox enzymes, and mixtures thereof.

4. The hair treatment composition according to claim 1, wherein the composition is substantially free of ammonia.

5. The hair treatment composition according to claim 1, wherein the composition is capable of being mixed with an oxidizing composition comprising: (i) at least one oxidizing agent selected from peroxides, urea peroxide, alkali metal bromates, ferricyanides, peroxygenated salts, perborates, percarbonates, laccases, peroxidases, redox enzymes, and mixtures thereof; and (ii) a cosmetically acceptable solvent selected from water and a water/organic solvent mixture.

6. The hair treatment composition according to claim 1, further comprising a colorant selected from oxidative dye precursors, direct dyes, pigments, and mixtures thereof.

7. A composition for altering the color of hair comprising:
A. a hair treatment composition consisting essentially of:
  (a) about 3% by weight of a crosslinked (meth)acrylic acid/ethyl acrylate copolymer selected from an acrylates copolymer in the form of an aqueous dispersion;
  (b) from about 0.1% to about 0.25% by weight of at least one carbomer compound chosen from homopolymers of acrylic acid crosslinked with an allyl ether of pentaerythritol, an allyl ether of sucrose, or an allyl ether of propylene;
  (c) from about 1% to about 1.25% by weight of at least one fatty alcohol that is liquid at room temperature and at atmospheric pressure and selected from lauryl alcohol, oleyl alcohol, caprylic alcohol, or mixtures thereof;
  (d) about 50% by weight of at least one fatty substance other than (c) selected from mineral oils;
  (e) about 0.55% by weight of at least one anionic surfactant selected from sulfate anionic surfactants, or mixtures thereof;
  (f) about 3% by weight of at least one amphoteric surfactant selected from sodium cocoamphoacetate;
  (g) from about 5% to about 6% by weight, of at least one basic compound selected from ethanolamine;
  (h) at least one cosmetically acceptable solvent selected from water and a water/organic solvent mixture; all weights being based on the total weight of the composition; and
B. an oxidizing composition containing at least one oxidizing agent selected from peroxides, urea peroxide, alkali metal bromates, ferricyanides, peroxygenated salts, perborates, percarbonates, laccases, peroxidases, redox enzymes, and mixtures thereof, and a cosmetically acceptable solvent selected from water and a water/organic solvent mixture.

8. The composition for altering the color of hair of claim 7, wherein the hair treatment composition further comprises at least one colorant compound selected from oxidative dye precursors, direct dyes, pigments, and mixtures thereof.

9. A process for altering the color of hair, comprising contacting hair with a composition for altering the color of hair for a sufficient period of time to achieve a desired level of lift of the color of the hair and/or alteration of the color of hair; wherein the composition is formed from mixing the hair treatment composition of claim 1 with an oxidizing composition containing at least one oxidizing agent selected from peroxides, urea peroxide, alkali metal bromates, ferricyanides, peroxygenated salts, perborates, percarbonates, laccases, peroxidases, redox enzymes, and mixtures thereof and a cosmetically acceptable solvent selected from water and a water/organic solvent mixture.

10. The process according to claim 7, wherein the hair treatment composition further comprises at least one colorant compound selected from oxidative dye precursors, direct dyes, pigments, and mixtures thereof.

11. A multi-compartment kit for altering the color of hair comprising:
A. a first compartment containing a hair treatment composition consisting essentially of:
  (a) about 3% by weight of at least one polymer chosen from acrylates copolymer selected from crosslinked copolymers of (meth)acrylic acid and ethyl acrylate;
  (b) from about 0.1% to about 0.25% by weight of at least one carbomer compound chosen from homopolymers of acrylic acid crosslinked with an allyl ether of pentaerythritol, an allyl ether of sucrose, or an allyl ether of propylene;
  (c) from about 1% to about 1.25% by weight of at least one fatty alcohol that is liquid at room temperature and at atmospheric pressure and chosen from lauryl alcohol, oleyl alcohol, caprylic alcohol, or mixtures thereof;
  (d) about 50% by weight of at least one fatty substance other than (c) chosen from mineral oils;
  (e) about 0.55% by weight of at least one anionic surfactant chosen from sodium lauryl sulfate;
  (f) about 3% by weight of at least one amphoteric surfactant chosen from sodium cocoamphoacetate;
  (g) from about 5% to about 6% by weight of at least one basic compound selected from ethanolamine;
  (h) at least one cosmetically acceptable solvent selected from water and a water/organic solvent mixture; and
  (i) about 2.4% by weight of at least one colorant selected from oxidative dye precursors;
all weights being based on the total weight of the composition; and
B. a second compartment containing an oxidizing composition comprising at least one oxidizing agent selected from peroxides, urea peroxide, alkali metal bromates, ferricyanides, peroxygenated salts, perborates, percarbonates, laccases, peroxidases, redox enzymes, and mixtures thereof, and a cosmetically acceptable solvent selected from water and a water/organic solvent mixture.

* * * * *